United States Patent [19]

Goldring et al.

[11] Patent Number: 5,516,651

[45] Date of Patent: May 14, 1996

[54] NUCLEIC ACIDS ENCODING CALCITONIN RECEPTOR AND USES THEREOF

[75] Inventors: Steven R. Goldring, Auburndale; Alan H. Gorn, Boston; Herb Y. Lin, Cambridge, all of Mass.

[73] Assignee: The General Hospital Corporation, Boston, Mass.

[21] Appl. No.: 792,885

[22] Filed: Nov. 15, 1991

[51] Int. Cl.$^6$ .............................. C12P 21/06; C12N 5/00; C12N 15/00; C07H 17/00

[52] U.S. Cl. ...................... 435/69.1; 435/6; 435/240.6; 435/320.1; 536/23.1; 536/23.5; 935/22; 935/33; 935/66; 935/70

[58] Field of Search ........................ 536/27, 23.5, 23.1; 435/320.1, 240.2, 252.8, 6, 69.1, 252.3; 935/33, 22, 66, 70

[56] References Cited

U.S. PATENT DOCUMENTS 4,962,035  10/1990  Leder et al. ............................ 475/320

OTHER PUBLICATIONS

Biochem. J. 250:877–882, 1988.

Lin et al. Science 254:1022–1024, 1991.

Goldring et al., 1978, *Biochem. and Biophys. Res. Comm.*, 83:434–440, "A Cell Strain Cultured from Porcine Kidney Increases Cyclic AMP Content Upon Exposure to Calcitonin or Vasopressin".

Upchurch et al., 1986, *Journal of Bone and Mineral Research*, 1:299–304, "Differential Cyclic AMP Responses to Calcitonin Among Human Ovarian Carcinoma Cell Lines: A Calcitonin-Responsive Line . . . Rare Tumor Type".

Devereux et al., 1984, *Nucleic Acids Research*, 12:387–395, "A Comprehensive Set of Sequence Analysis Programs for the Vax".

von Heijne, 1986, *Nucleic Acids Research*, 14:4683–4690, "A New Method for Predicting Signal Sequence Cleavage Sites".

Gearing et al., 1989, *The EMBO Journal*, 8:3667–3676, "Expression Cloning of a Receptor for Human Granulocyte-Macrophage Colony-Stimulating Factor".

Lin et al., 1991, *Proc. Natl. Acad. Sci. USA*, 88:3185–3189, "Cloning and Functional Expression of a Vascular Smooth Muscle Endothelin 1 Receptor".

Attwood et al., 1991 *Gene*, 98:153–159, "Multiple Sequence Alignment of Protein Families Showing Low Sequence Homology: . . . Approach using Database Pattern-Matching Discriminators for G–Protein–Linked Receptors".

Moll et al., 1983, *Laboratory Investingation*, 49:599–610, "Cytokeratins of Normal Epithelia and Some Neoplasms of the Female Genital Tract".

Ishihara et al., 1991, *EMBOJ*, 10:1635–1641, "Molecular Cloning and Expression of a CDNA Encoding the Secretin receptor".

Dickersin et al., 1982, *Cancer*, 49:188–197, "Small Cell Carcinoma of the Ovary with Hypercalcemia: A Report of Eleven Cases".

Copp et al., 1962, *Endocrinology*, 70:638–649, "Evidence for Calcitonin—A New Hormone from the Parathyroid that Lowers Blood Calcium".

Haas et al., 1971, *The Journal of Clinical Investigation*, 50:2689–2702, "Renal Effects of Calcitonin and Parathyroid Extract in Man: Studies in Hypoparathyroidism".

Friedman and Raisz, 1965, *Science*, 150:1465–1467, "Thyrocalcitonin: Inhibitor of Bone Resorption in Tissue Culture".

Warshawsky et al., 1980, *J. Cell Biology*, 85:682–694, "Direct in Vivo Demonstration by Radioautography of Specific Binding Sites for Calcitonin in Skeletal and Renal Tissues of the Rat".

Goldring et al., 1987, *J. Clin Invest*, 79:483–491, "Human Giant Cell Tumors of Bone Identification and Characterization of Cell Types".

Murad et al., 1970, *Proceedings of the National Academy of Science*, 65:446–453, "Effect of Thyrocalcitonin on Adenosine 3':5'-cyclic Phosphate Formation by Rat Kidney and Bone".

Marshall et al., 1985, *The Journal of Biological Chemistry*, 260:4128–4135, "Stoichiometric Translocation of Adipocyte Insulin Receptors from the Cell-Surface to the Cell-Interior".

Wohlwend et al., 1985, *Biochem. and Biophys. Res. Comm.*, 131:537–542, "Calcitonin and Calcitonin Gene–Related Peptide Interact with the Same Receptor in Cultureed LLC–PK1 Kidney Cells".

Zhu et al., 1991, *Biochem. and Biophys. Res. Comm.*, 177:771–776, "Amylin Increases Cyclin AMP Formation in L6 Myocytes through Calcitonin Gene–Related Peptide Receptors".

Juppner et al., 1991, *Science*, 254:1024–1026, "A G Protein–Linked Receptor for Parathyroid Hormone and Parathyroid Hormone–Related Peptide".

Zaidi et al., 1990, *Journal of Endocrinology*, 126:473–481, "Evidence that the Action of Calcitonin on Rat Osteoclasts is Mediated by Two G Proteins Acting via Separate Post-Receptor Pathways".

Chakraborty et al., 1991, *Science*, 251:1078–1082, "Cell Cycle–Dependent Coupling of the Calcitonin Receptor to Different G Proteins".

*Primary Examiner*—Margaret Parr
*Assistant Examiner*—Bradley L. Sisson
*Attorney, Agent, or Firm*—Fish & Richardson

[57] ABSTRACT

Recombinant DNA which encodes a calcitonin receptor polypeptide, vectors and hosts containing the recombinant DNA, and methods for expressing a calcitonin receptor polypeptide from the recombinant DNA are described.

10 Claims, 14 Drawing Sheets

```
CTR   1    MRFTLTRWCLTLFIFINRPLPVLPDSADGAHTPTLEPEPFIYILGKQ...
OKO   1    ..MGAPRISHSLALLICCSVLSSVYALVDADDVITKEEQIILRNAQAQC

CTR  48    ........RMLEAQHRCYDRM............QKLPPYQGE........
OKO  49    EQRLKEVLRVPELAESAKDWMSRSAKTKKEKPAEKLYPQAEESREVSDRS

+              +              +                  +
CTR  74    ...GLYCNRTWDGWSCWDDTPAGVLAEQYCPDYFPDFDAAEKVTKYCGED
OKO  99    RLQDGFCLPEWDNIVCWPAGVPGKVVAVPCPDYFYDFNHKGRAYRRCDSN

#    #    +                              I
CTR 117    GDWYRHPESNISWSNYTMCNAFTPDKLQNAYILYYLAI...VGHSLSILT
OKO 149    GSWELVPGNNRTWANYSECVKFLTNETREREVFDRLGMIYTVGYSISLGS

II
CTR 164    LLISLGIFMFLRSISCQRVTLHKNMFLIYMLNSIIIVHLVVI...VPNG
OKO 199    LTVAVLILGYFRRLHCIRNYIHMHLFVSFMLRAVSIFIKDAVLYSGVSTD

+
CTR 211    ELVK..........RDPPI.........CKVLHFFHQYMMSCNYFWMLCEGV
OKO 249    EIERITEEELRAFTEPPPADKAGFVGCRVAVTVFLYFLTNYYWILVEGL
                III                          IV
                                                              +
CTR 244    YLHTLIVVSVFAEGQRLWWYHVLGWGFPLIPTTAHAITRAMLFNDNCWLS
OKO 299    YLHSLIFMAFFSEKKYLWGFTLFGWGLPAVFVAVWVTVRATLANTECWDL
                                 V
CTR 294    VDTNLLYIIHGPVMAALVVNFFFLLNILRVLVKKLKESQEAES...HMYL
OKO 349    SSGNKKWIIQVPILAAIVVNFILFINIIRVLATKLRETNAGRCDTRQQYR
                       VI                                    VII
CTR 342    KAVRATLILVPLLGVQFVVLPWRHSTPLIGKIYDYVVH...SLIHFQGFF
OKO 399    KLLKSTLVLMPLFGVHYIVRMATPYLEVSGILWQVQMHYEMLFNSFQGFF

CTR 388    VAIIYCFCNHEVQGALKRQWNQY....QAQRWA.................
OKO 449    VAIIYCFCNGEVQAEIKKSWSRWTLAIDFKRKARSGSSTYSYGPMVSHTS

CTR 417    ....GRRSTRAANAAAATAAAAAALAETV.EIPVYICHQEPREE...PAG
OKO 499    VTNVGPRGGIALSLSPRIAPGAGASANGHHQLPGYVKHGSISENSLPSSG

CTR 459    EEPVVEVEG............VEVIAMEVLEQETSA..............
OKO 549    PEEGTKDDGYLNGSGLYEPMVGEQPPPLLEEERETVM..............
```

FIG. 3

```
GTGCGCACGT CCGCACCTCA CCCTGCGGCT GACATCTCCT GCCCAGGAGA TGGGCGCTGA    60

AGCTTGAGCG CCTGAGTCCC TGGAGCCACA CCTGCGAACA CCCTTTGCTT CTATTGAGCT   120

GTGCCCAGCC GCCCAGTGAC AGAATTCCAG AATAAATGAT TCCCACTGAT CCACCCACTT   180

TTGCCACCCC AGGATGCAAT TTTCTGGAGA AGAGATTAGT GGACAAAGAG ATCTTCAAAA   240

ATCAAAA                                                             247
```

```
ATG AGG TTC ACA TTT ACA AGC CGG TGC TTG GCA CTG TTT CTT CTT CTA    295
Met Arg Phe Thr Phe Thr Ser Arg Cys Leu Ala Leu Phe Leu Leu Leu
1             5                   10                  15

AAT CAC CCA ACC CCA ATT CTT CCT GCC TTT TCA AAT CAA ACC TAT CCA    343
Asn His Pro Thr Pro Ile Leu Pro Ala Phe Ser Asn Gln Thr Tyr Pro
            20              25                  30

ACA ATA GAG CCC AAG CCA TTT CTT TAC GTC GTA GGA CGA AAG AAG ATG    391
Thr Ile Glu Pro Lys Pro Phe Leu Tyr Val Val Gly Arg Lys Lys Met
        35              40              45

ATG GAT GCA CAG TAC AAA TGC TAT GAC CGA ATG CAG CAG TTA CCC GCA    439
Met Asp Ala Gln Tyr Lys Cys Tyr Asp Arg Met Gln Gln Leu Pro Ala
50              55              60

TAC CAA GGA GAA GGT CCA TAT TGC AAT CGC ACC TGG GAT GGA TGG CTG    487
Tyr Gln Gly Glu Gly Pro Tyr Cys Asn Arg Thr Trp Asp Gly Trp Leu
65              70              75              80

TGC TGG GAT GAC ACA CCG GCT GGA GTA TTG TCC TAT CAG TTC TGC CCA    535
Cys Trp Asp Asp Thr Pro Ala Gly Val Leu Ser Tyr Gln Phe Cys Pro
                85                  90                  95

GAT TAT TTT CCG GAT TTT GAT CCA TCA GAA AAG GTT ACA AAA TAC TGT    583
Asp Tyr Phe Pro Asp Phe Asp Pro Ser Glu Lys Val Thr Lys Tyr Cys
            100             105                 110

GAT GAA AAA GGT GTT TGG TTT AAA CAT CCT GAA AAC AAT CGA ACC TGG    631
Asp Glu Lys Gly Val Trp Phe Lys His Pro Glu Asn Asn Arg Thr Trp
        115             120                 125

TCC AAC TAT ACT ATG TGC AAT GCT TTC ACT CCT GAG AAA CTG AAG AAT    679
Ser Asn Tyr Thr Met Cys Asn Ala Phe Thr Pro Glu Lys Leu Lys Asn
130             135                 140

GCA TAT GTT CTG TAC TAT TTG GCT ATT GTG GGT CAT TCT TTG TCA ATT    727
Ala Tyr Val Leu Tyr Tyr Leu Ala Ile Val Gly His Ser Leu Ser Ile
145             150                 155                 160

TTC ACC CTA GTG ATT TTC CTG GGG ATT TTC GTG TTT TTC AGA AAA TTG    775
Phe Thr Leu Val Ile Phe Leu Gly Ile Phe Val Phe Phe Arg Lys Leu
                165             170                 175
```

FIG. 8-1

```
ACA ACT ATT TTT CCT TTG AAT TGG AAA TAT AGG AAG GCA TTG AGC CTT     823
Thr Thr Ile Phe Pro Leu Asn Trp Lys Tyr Arg Lys Ala Leu Ser Leu
        180                 185                 190

GGC TGC CAA AGG GTA ACC CTG CAC AAG AAC ATG TTT CTT ACT TAC ATT     871
Gly Cys Gln Arg Val Thr Leu His Lys Asn Met Phe Leu Thr Tyr Ile
        195                 200             205

CTG AAT TCT ATG ATT ATC ATC ATC CAC CTG GTT GAA GTA GTA CCC AAT     919
Leu Asn Ser Met Ile Ile Ile Ile His Leu Val Glu Val Val Pro Asn
────210──────────────── ────215──────── ────220────
                                II

GGA GAG CTC GTG CGA AGG GAC CCG GTG AGC TGC AAG ATT TTG CAT TTT     967
Gly Glu Leu Val Arg Arg Asp Pro Val Ser Cys Lys Ile Leu His Phe
─225┘               230                 235                 240

TTC CAC CAG TAC ATG ATG GCC TGC AAC TAT TTC TGG ATG CTC TGT GAA    1015
Phe His Gln Tyr Met Met Ala Cys Asn Tyr Phe Trp Met Leu Cys Glu
                245                 250             ──255──

GGG ATC TAT CTT CAT ACA CTC ATT GTC GTG GCT GTG TTT ACT GAG AAG    1063
Gly Ile Tyr Leu His Thr Leu Ile Val Val Ala Val Phe Thr Glu Lys
──────────────260──────────── ──265──────── ────270──────────┘
                        III

CAA CGC TTG CGG TGG TAT TAT CTC TTG GGC TGG GGG TTC CCG CTG GTG    1111
Gln Arg Leu Arg Trp Tyr Tyr Leu Leu Gly Trp Gly Phe Pro Leu Val
        275             └280                 ──285────────

CCA ACC ACT ATC CAT GCT ATT ACC AGG GCC GTG TAC TTC AAT GAC AAC    1159
Pro Thr Thr Ile His Ala Ile Thr Arg Ala Val Tyr Phe Asn Asp Asn
────290──────── ──────295────────────── ────300┘
            IV

TGC TGG CTG AGT GTG GAA ACC CAT TTG CTT TAC ATA ATC CAT GGA CCT    1207
Cys Trp Leu Ser Val Glu Thr His Leu Leu Tyr Ile Ile His Gly Pro
305                 310         └───315────────── ────320─

GTC ATG GCG GCA CTT GTG GTC AAT TTC TTC TTT TTG CTC AAC ATT GTC    1255
Val Met Ala Ala Leu Val Val Asn Phe Phe Phe Leu Leu Asn Ile Val
            ──── 325 ──── ────330──── ──── 335──
                                    V

CGG GTG CTT GTG ACC AAA ATG AGG GAA ACC CAT GAG GCG GAA TCC CAC    1303
Arg Val Leu Val Thr Lys Met Arg Glu Thr His Glu Ala Glu Ser His
            ──── 340┘       345                 350

ATG TAC CTG AAG GCT GTG AAG GCC ACC ATG ATC CTT GTG CCC CTG CTG    1351
Met Tyr Leu Lys Ala Val Lys Ala Thr Met Ile Leu Val Pro Leu Leu
            355         └360 ──────── ────365────────

GGA ATC CAG TTT GTC GTC TTT CCC TGG AGA CCT TCC AAC AAG ATG CTT    1399
Gly Ile Gln Phe Val Val Phe Pro Trp Arg Pro Ser Asn Lys Met Leu
──── 370 ──────────── ────375────        380
        VI

GGG AAG ATA TAT GAT TAC GTG ATG CAC TCT CTG ATT CAT TTC CAG GGC    1447
Gly Lys Ile Tyr Asp Tyr Val Met His Ser Leu Ile His Phe Gln Gly
385                 390             └──395──────── ────────400─
```

FIG. 8-2

```
TTC TTT GTT GCG ACC ATC TAC TGC TTC TGC AAC AAT GAG GTC CAA ACC    1495
Phe Phe Val Ala Thr Ile Tyr Cys Phe Cys Asn Asn Glu Val Gln Thr
            ─── 405 ─────────── 410 ───┘        415
         VII

ACC GTG AAG CGC CAA TGG GCC CAA TTC AAA ATT CAG TGG AAC CAG CGT    1543
Thr Val Lys Arg Gln Trp Ala Gln Phe Lys Ile Gln Trp Asn Gln Arg
        420             425             430

TGG GGG AGG CGC CCC TCC AAC CGC TCT GCT CGC GCT GCA GCC GCT GCT    1591
Trp Gly Arg Arg Pro Ser Asn Arg Ser Ala Arg Ala Ala Ala Ala Ala
        435             440             445

GCG GAG GCT GGC GAC ATC CCA ATT TAC ATC TGC CAT CAG GAG CCG AGG    1639
Ala Glu Ala Gly Asp Ile Pro Ile Tyr Ile Cys His Gln Glu Pro Arg
        450             455             460

AAT GAA CCA GCC AAC AAC CAA GGC GAG GAG AGT GCT GAG ATC ATC CCT    1687
Asn Glu Pro Ala Asn Asn Gln Gly Glu Glu Ser Ala Glu Ile Ile Pro
465             470             475             480

TTG AAT ATC ATA GAG CAA GAG TCA TCT GCT                            1717
Leu Asn Ile Ile Glu Gln Glu Ser Ser Ala
                485             490

TGAATGTGAA GCAAACACAG TATCGTGATC ACTGAGCCAT CATTTCCTGG GAGAAAGACC  1777
ATGCATTTAA AGTATTCTCC ATCCTCCCAG GAACCGAACA TATCATTTGT GAAGAATTAT  1837
TCAGTGAATT TGTCCATTGT AAATCTGAAG AAAGTTATTC TTGGTACTGT TGCTTTGGGA  1897
GACAGTCTAG GAATGGAGTC TCCCACTGCA ACTTGTGAAC TCCATCATTC ATCCAGGACT  1957
GAGATGCAAA TGTCACAGTA ATGCAAGCAA AGTATCAAAG AAAAACAATG AAATTGACCT  2017
AGTTCAGATA CAGGGTGCTC CTTGTCAATA CTGAGCCATT TATACCTTTG AAATATTAAA  2077
ATCACTGTCA ATATTTTTAT TTTTAACTCT GGATTTTGAA TTAGATTATT TCTGTATTTG  2137
GCTATGGATC TGATTTTTAA TTTTTTTAAA TTTCAGTCAA TTCTGATGTT ACTGAGATGT  2197
TTTACCATCC TTACAATGTA AACCACATGA ACTACGTGAC CTCTGCAAGA CAAAGCGGCT  2257
TTCTAATAGA GAGATTAGTA AATATGTGAA GAAAAAGACC TGCATTTGGC AGGAAGATGT  2317
ATGCTTTGAA TGCAAAAGAA ATTTAGAGTC AATTTGCTGA AAACATTACA TGCTCAGCTT  2377
GGTTTTGGAC AAGCCTGTCC ATTGGGCAGG ACCTAGCTGT TGTAAAGAAT TGGTCTTAAT  2437
GTTGAATGTA TTTTGGTTGC TGATGTTTAT AAACTGAGAG GTCACAAAGA ATCTATCACT  2497
AAAAATTTTT ACAAAACTGC CAAAAATATA ATTCTTAGTG GAAGACAATA CTCCCTTTAA  2557
AGAAAGAGAG TTTGCCACTC CCTAAACTC CAGGATTTAT AAAGCAAATT ACTCCAAGGT   2617
```

FIG. 8-3

```
TTATAAAGCA GATTACCTCT TGCCCTTGGG TGCTATCTAG CAGTAAAAGA TAAATTTGTT 2677
GAATATTGGT AATTAAAAGA CTCCACATAA GTCCATTAAC TGCTTTCCAC CCAGCTTCAA 2737
AGCTTAAAAA GAGCTCAGGC TTTTCCAGGA AGATCCAGGA CGGCTAATTA GAAATCAACT 2797
TGTGGTTGAC CGCTTGTTTC TTGTTATTAC CAAAACAGGA GGGGAAAAAA TTAACTGCTC 2857
CAAATTTAAC CATAAATCAA TTCATGTTTA ACGTTCTCA TTAAAATCCA GTATTATATT 2917
ATCATATCTC TCTTTACTTC CCAGTATAAG ATTTTTGAAA ATCCTGAATA AACCAGTATC 2977
GTTACTGGCA CCTGAAATTA ATTTGTGAAT TGCAACAGT AATCAGAGTT ACCATTATTT 3037
AATTTGTATG CTAAATGAGG AGGTACATTG AAACCCTCCA AATCTCCAGT CTCATCTATG 3097
TCATATTTTG CCACTGCCTT TCAGAAGTGA TTTAGTTGTG GAAAGATAAT AAATTGATTT 3157
GTTATGGTTA CATATTCAGC GCACGCAGAG AAAATTAATT ATATTTCTAC AGAGAAAATG 3217
AATTTGGGAT ACTAAAGTAG TTTAAGTCTC CTTTACTGAA TGTAAGGGGG GGATCGAAAA 3277
GAAGGTATTT TTCCAATCAC AGTGTTATGT AGTATTGTTC TATTTTTGTT TACAAACATG 3337
GAAAACAGAG TATTTCTGGC AGCTCTCGTA CAAATGTGAT AATATATTGC TAAAATATTT 3397
TAGATGTTAT TATGCTAATA TAGTAGGGGT TGAAGAAAAC AAAATAGCTT ATTATAGAAT 3457
TGCACATAGT TCTGCCCAAA TTATGTGAAA TGCTTATGCT TGTGTATATG TATAAATTAA 3517
TACACACTAC GTTAAAAGCA AAAAGATGTA TATTTGCATA TTTTTCTAAA GAAATATATT 3577
ATTCATCTTT T                                                  3588
```

FIG. 8-4

NUCLEIC ACIDS ENCODING CALCITONIN RECEPTOR AND USES THEREOF

Partial funding for the work described herein was provided by the U.S. Government, which has certain rights in the invention.

BACKGROUND OF THE INVENTION

The invention relates to the field of receptors for peptide hormones such as calcitonin.

Calcitonin is a peptide hormone of 32 amino acids that was initially identified as a hypocalcemic factor secreted by the parafollicular cells of the thyroid gland in response to elevations in serum calcium (Copp et al., 1962, Endocrinology 70:638–649). The hypocalcemic effect of calcitonin is mediated primarily by direct inhibition of osteoclast-mediated bone resorption (Friedman and Raisz, 1965, Science 150:1465–1467; Warshawsky et al., 1980, J. Cell Biol. 85:682–694). Calcitonin also enhances renal calcium excretion (Haas et al., 1971, J. Clin. Invest. 50:2689–2702; Warshawsky et al., Supra). In addition to receptors in bone and kidney, high affinity calcitonin binding sites have been demonstrated in many different tissues including the central nervous system, testes, placenta, lung, and on spermatozoa. Cells derived from lung and breast carcinomas, as well as certain lymphoid and myeloid cell lines also express receptors for this hormone. Although the physiologic role of calcitonin in many of these tissues remains poorly understood, its action clearly extends beyond its effects on calcium homeostasis.

The unique ability of calcitonin to inhibit osteoclast-mediated bone resorption has led to its wide-spread use in the treatment of disorders of bone-remodelling, including osteoporosis, Paget's disease of bone and some forms of hypercalcemia of malignancy. In addition, calcitonin has been used in studies to treat pancreatitis and peptic ulcer disease, and to produce centrally mediated analgesia. It has not been established whether all of the pharmacological effects of calcitonin are mediated directly by high affinity calcitonin receptors in these target tissues, or whether they are related to the cross-reaction of calcitonin with receptors for other hormones such as α or β calcitonin gene related peptide (CGRP) (Wohlwend et al., 1985, Biochem. Biophys. Res. Comm. 131:537–542), or amylin (Zhu et al., 1991, Biochem. Biophys. Res. Comm. 177:771–776), which share similarity in amino acid sequence with calcitonin. αCGRP is a product of the calcitonin gene produced by differential RNA splicing. βCGRP is a product of a separate gene but differs from αCGRP by only a single amino acid. These related ligands most likely interact primarily with their own high affinity receptors to produce hormone-specific effects, but at very high concentrations may also cross react with the receptors for the other peptides.

SUMMARY OF THE INVENTION

The invention features a recombinant DNA which encodes a calcitonin receptor polypeptide; the recombinant DNA is preferably a cDNA encoding porcine or human calcitonin receptor polypeptide.

The recombinant DNA can be used to test a compound to determine whether it is capable of binding to a calcitonin receptor; the method involves a) providing a recombinant eukaryotic cell which is transfected with DNA encoding calcitonin receptor and which is capable of expressing calcitonin receptor on its surface; b) contacting the cell with the test compound; and c) detecting binding of the cell with the test compound as an indication of binding of the compound to the receptor.

The recombinant DNA can also be used to test a compound to determine whether it is capable of binding to a calcitonin receptor; the method involves a) mixing calcitonin receptor with labeled calcitonin and the test compound, and b) measuring the amount of label bound to the receptor as an indication of binding of the test compound to the receptor.

In preferred embodiments, the recombinant DNA encodes a receptor which is a mammalian calcitonin receptor, most preferably from a pig or a human.

In other preferred embodiments, the cell in which the recombinant DNA is expressed is a cell that does not express on its surface any other proteins capable of binding to calcitonin receptor.

In yet other preferred embodiments, the method of testing compounds further comprises the step of determining whether the test compound exhibits in its interaction with the cell a biological activity of calcitonin, most preferably this activity is an increased level of intracellular cyclic AMP, or an increased intracellular concentration of calcium.

The invention also features recombinant calcitonin receptor polypeptide expressed from the recombinant DNA, wherein the polypeptide is most preferably porcine or human calcitonin receptor polypeptide.

The invention includes a vector comprising recombinant DNA which is capable of directing the expression of a polypeptide encoded by the DNA in the vector-containing cell.

The invention also includes a method of producing a recombinant calcitonin receptor polypeptide, the method comprising, a) providing a recombinant cell transformed with DNA encoding calcitonin receptor polypeptide positioned for expression in the cell; b) culturing the transformed cell under conditions for expressing the DNA; and c) isolating the recombinant polypeptide.

The invention also features an antibody which binds preferentially to a calcitonin receptor polypeptide, and a method of using the antibody to identify other calcitonin receptors in cells from tissues.

The invention also includes a method of identifying other calcitonin receptors in cells from tissues by screening a bacterial library expressing RNA specific for that tissue with a recombinant DNA encoding calcitonin receptor, or a portion thereof of greater than or equal to 30 base pairs, which contains an identifying region unique to calcitonin receptor, and detecting hybridization of the probe to the bacterial cells as an indication that the bacterial cells express RNA specific for calcitonin receptor.

Calcitonin receptor, as used herein, means any receptor in any organ or tissue to which calcitonin preferentially binds, including receptors that are related to, but not identical to, calcitonin receptor.

Recombinant DNA, as used herein, means DNA which is separated from other DNA with which it is naturally joined covalently.

A vector, as used herein, is an autonomously replicating DNA molecule.

In the methods of the invention, compounds will be tested for their ability to bind to the calcitonin receptor and for their ability to exhibit biological activity. The methods rely upon the expression of calcitonin receptor on the surface of cells that do not naturally express such proteins on their surface.

The methods therefore have significant advantages over currently available methods, namely cells that naturally express calcitonin receptors, because they provide a clean assay, free of background binding activity, and wherein cross reactivity of compounds to calcitonin-like receptor molecules is eliminated.

The invention provides for the identification of new or existing compounds that exhibit biological activity of calcitonin. While calcitonin is available for the treatment of many diseases of humans, it cannot be administered orally. Newly identified compounds that exhibit biological activity of calcitonin may be orally available.

The antibody and calcitonin receptor-specific probes of the invention can be used to locate other calcitonin receptors within tissues of a mammal. Newly identified receptors can be used in the screening assay to identify yet other compounds that have biological activity of calcitonin that may be unique to specific tissues and organs in a mammal.

Other features and advantages of the invention will be apparent from the following detailed description, and from the claims.

DETAILED DESCRIPTION

The Drawings The drawings are first described.

FIGS. 1A and 1B are a composite of graphs depicting binding of porcine calcitonin to cells. FIG. 1A) Porcine calcitonin binding to LLC-PK$_1$ cells; FIG. 1B) Porcine calcitonin binding to COS cells transfected with cDNA encoding porcine CTR. Insets show Scatchard analysis of the binding data.

FIG. 2A is a histogram of the cAMP response in FIG. 2A) porcine calcitonin receptor-transfected COS cells and FIG. 2B) is a histogram of the cAMP response in COS cells mock-transfected with β-galactosidase. SCT=salmon calcitonin and ISO=isoproterenol.

FIG. 3 is the amino acid sequence of porcine CTR (SEQ ID NO:1) aligned with the PTH-PTHrP receptor. The alignment was generated with UWGCG program GAP (Devereux et al., 1984, Nucl. Acids Res. 12:387). Shaded boxes represent identity or similarity. The bars above the sequence represent the transmembrane domains. Symbol # indicates N-linked glycosylation sites and + indicates conserved cysteines.

FIG. 4A (low power) and FIG. 4B (high power) are emulsion autoradiographs of BIN-67 cells in culture following incubation with [$^{125}$I]-salmon calcitonin.

Figure 6A:
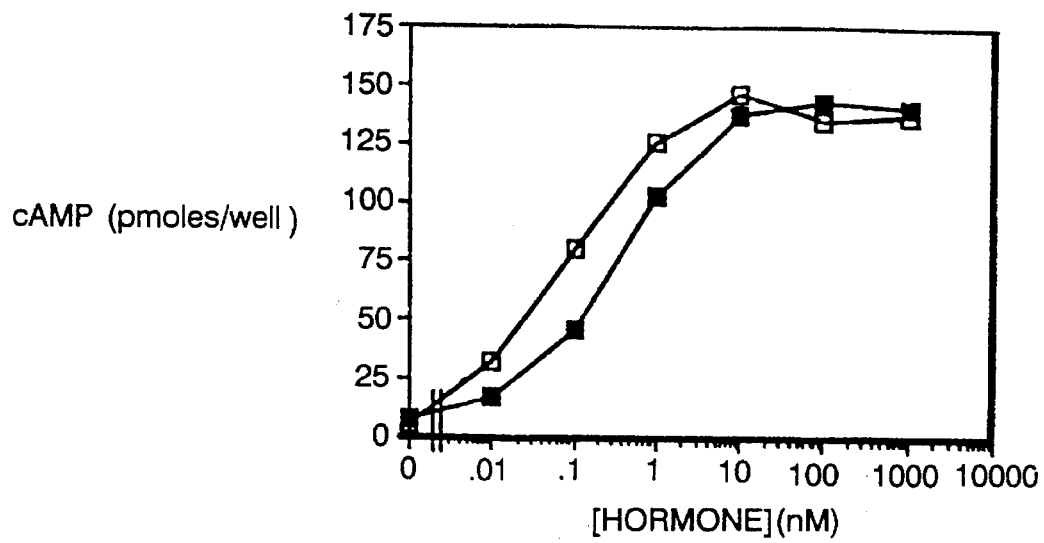
Figure 6B:
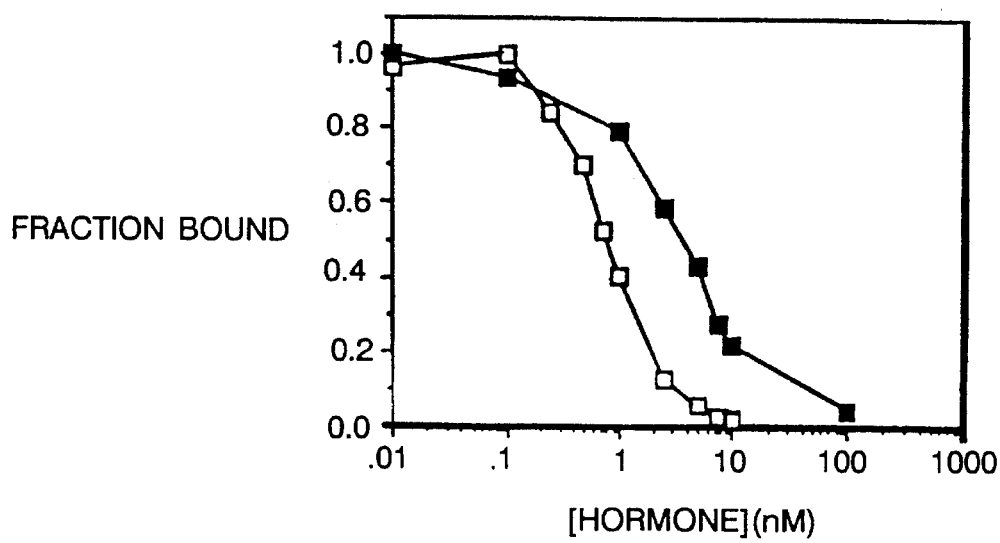
Figure 6C:
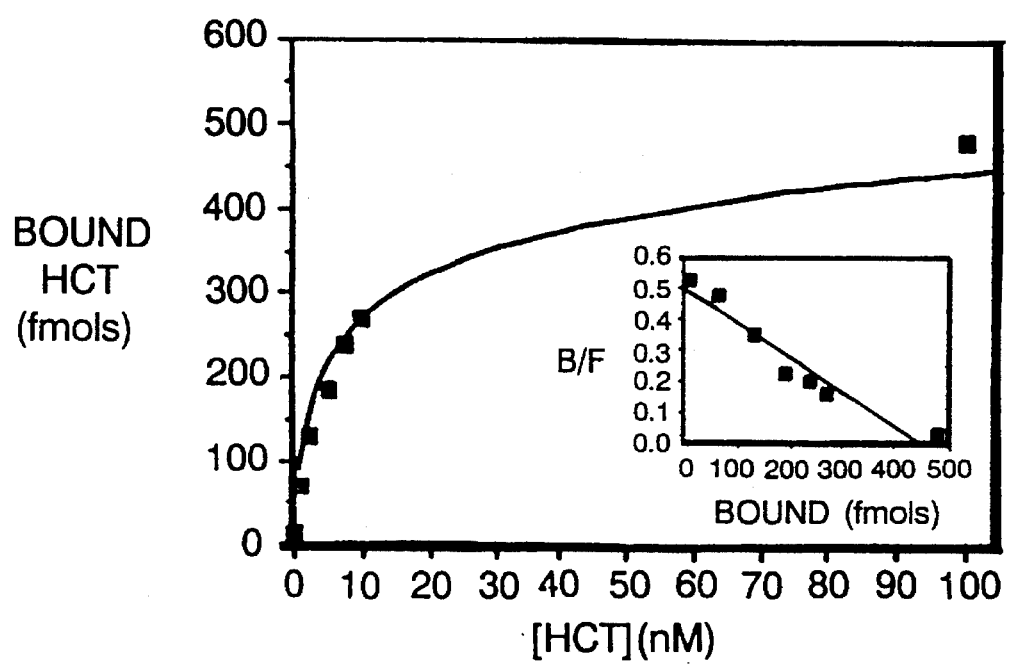

FIGS. 6A, 6B, and 6C are a composite of graphs of binding and cAMP dose response of human and salmon calcitonins in BIN-67 cells. FIG. 6A) cAMP dose response curves to salmon and human calcitonin; FIG. 6B) Competition dissociation binding curves for [$^{125}$I]-human calcitonin competed with unlabeled human calcitonin; FIG. 6C) Human calcitonin binding to BIN-67 cells. Maximal binding was 1.92×10$^4$ cpm per sample; the inset shows a Scatchard analysis of binding data.

Figure 7A:
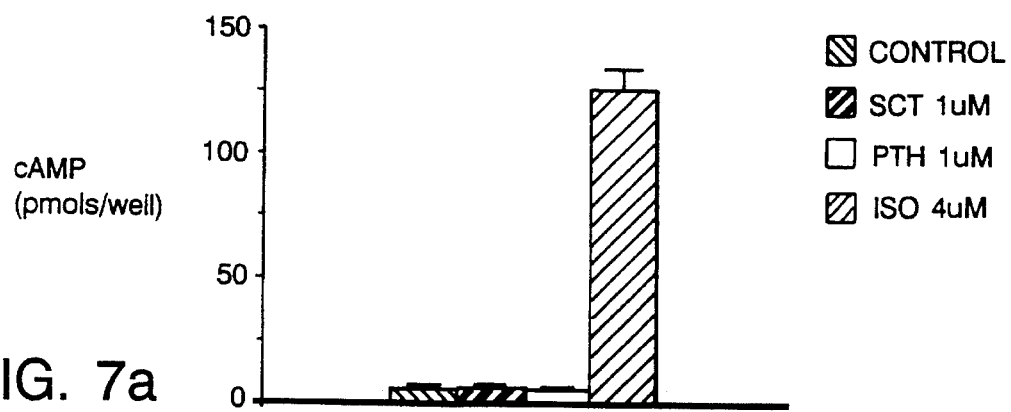
Figure 7B:
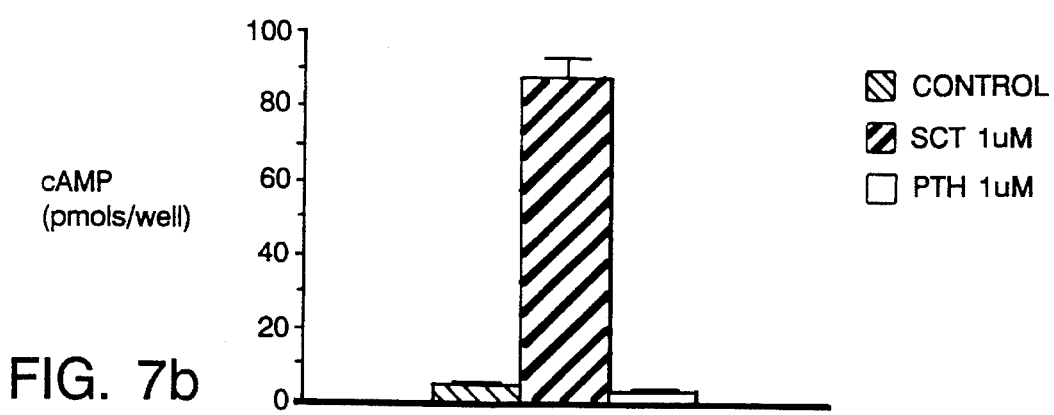
Figure 7C:
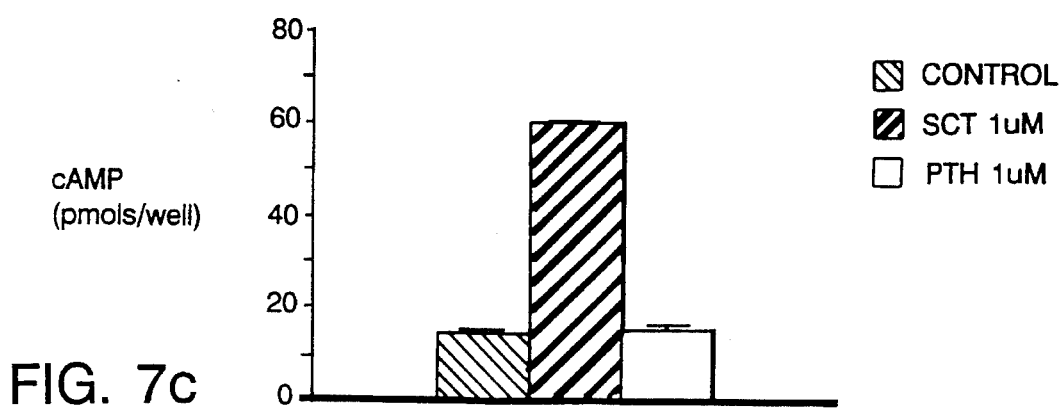

FIGS. 7A, 7B, and 7C are histograms representing the cAMP response in BIN-67 cells and in transfected COS cells. FIG. 7A) Mock (β-galactosidase) transfected COS cells; FIG. 7B) BIN-67 cells; FIG. 7C) COS cells transfected with human CTR cDNA.

FIGS. 8.1–8.3 is the nucleotide and predicted amino acid sequence of the human CTR cDNA clone (SEQ ID NO:2). The first underlined nucleotide triplet represents a potential initiation codon upstream of the assigned putative transcription start site. The arrow denotes a potential cleavage site (between bp 22 and 23) for a possible hydrophilic sequence. Four potential N-linked glycosylation sites are designated by the symbol #, and of those, the conserved sites are marked with the symbol *. Boxes mark extracellular cysteines. The seven putative hydrophilic membrane spanning domains are underlined.

Figure 9:
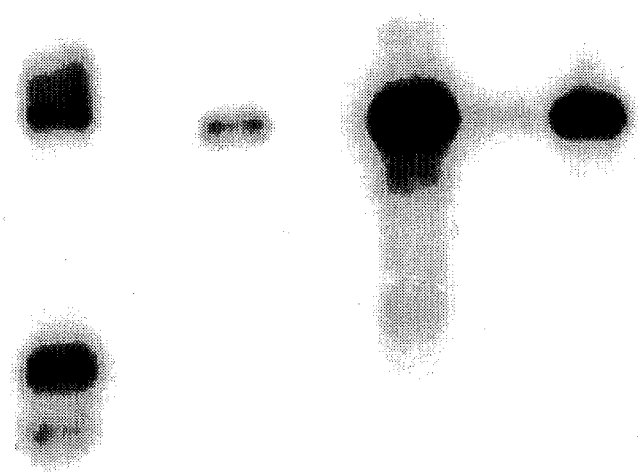

FIG. 9 is an autoradiogram of a northern blot hybridization experiment. Lane 1: 1 μg of LLC-PK$_1$ mRNA; Lane 2: 5 μg of BIN-67 cell mRNA; Lane 3: 5 μg of T-47D cell mRNA; Lane 4: 5 μg of human Giant Cell Tumor of bone mRNA. Size markers are on the left of the figure.

Cloning and Analysis of the cDNA Encoding a High Affinity Calcitonin Receptor from Porcine Cells.

Figure 1A:
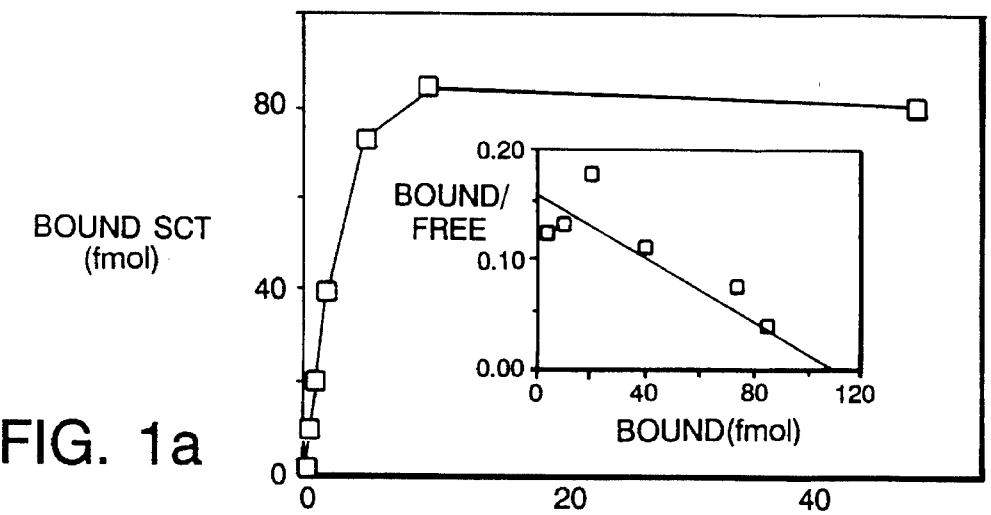

The porcine calcitonin receptor was cloned by expression in COS cells, using a strategy generally described in Lin et al., 1991, Proc. Natl. Acad. Sci. USA 88:3185. A size-fractionated cDNA library was constructed from LLC-PK$_1$ cells (Goldring et al., 1978, Biochem. Biophys. Res. Comm. 83:434), a porcine kidney epithelial cell line that expresses approximately 3×10$^5$ calcitonin receptors per cell with an apparent dissociation constant (K$_d$) of approximately 3 nM (FIG. 1A). Pools of mini-prep cDNA (Sambrook et al., 1989, Molecular Cloning: A Laboratory Manual, Cold Spring Harbor Laboratory, N.Y.) containing 10$^4$ recombinants were transfected into COS cells and screened for binding to radioiodinated salmon calcitonin by emulsion autoradiography (Gearing et al., 1989, EMBO 8:3667). After screening 30 pools representing 3×10$^5$ clones, two positive pools were identified from which two positive clones with cDNA inserts 2.2 and 3.9 kb in length were isolated. The 2.2 kb clone (3JS-14-FI) was a truncated version of the 3.9 kb clone (2B5-0-I) but encoded the same open reading frame.

Expression and function of salmon calcitonin on transfected COS cells.

Figure 1B:
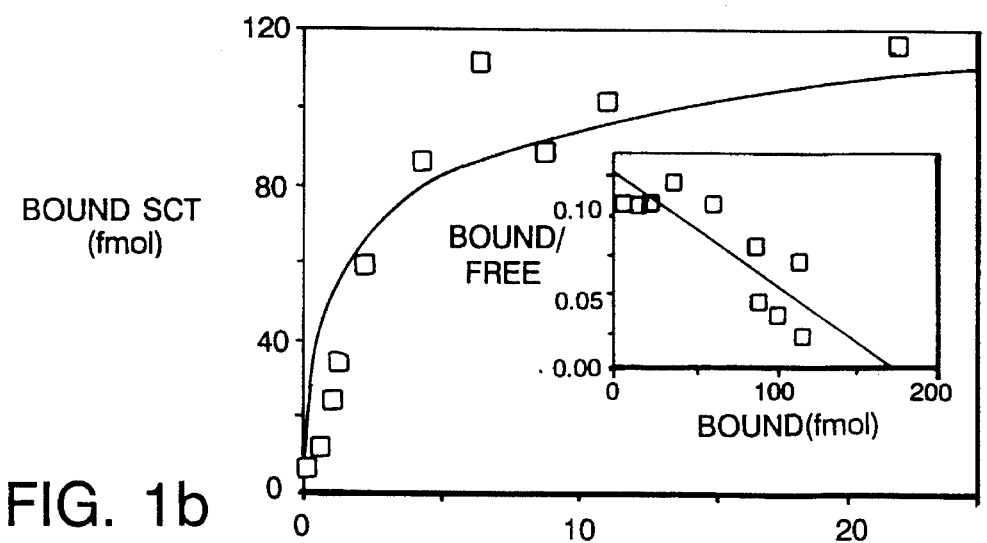

Radioiodinated salmon calcitonin binds to LLC-PK$_1$ cells and to COS cells transfected with the cloned porcine calcitonin receptor (CTR) cDNA (FIGS. 1A and 1B). Transfected COS cells expressed approximately 2×10$^6$ receptors per cell (assuming 10% of the cells expressed receptor) with an apparent K$_d$ of approximately 6 nM, similar to that expressed by LLC-PK$_1$ cells. Bovine parathyroid hormone (1–34) [PTH(1–34)] (Juppner et al., 1991, Science 254:1024) did not compete for binding of radioiodinated salmon calcitonin to the CTR transfectants.

Figures 2A, 2B:
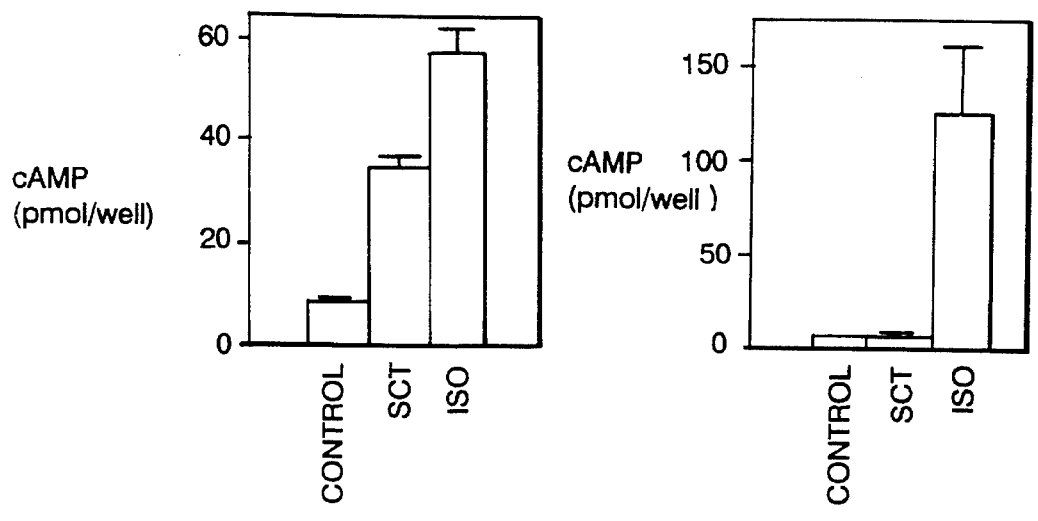

The cloned porcine receptor is functionally coupled to increased intracellular cAMP (FIGS. 2A and 2B). A 4-fold increase in the concentration of intracellular cAMP was observed after incubation of porcine CTR-transfected COS cells with calcitonin, but there was no increase when cells were transfected with β-galactosidase and subsequently stimulated with calcitonin. Isoproterenol, an agonist of the β-adrenergic receptor, activated adenylate cyclase in both β-galactosidase and porcine CTR-transfected cells.

RNA analysis.

Northern blot hybridization analysis of poly A$^+$ mRNA from LLC-PK$_1$ cells and pig organs demonstrated a single transcript of approximately 4.2 kb. Expression of this mRNA was most abundant in the brain but was also present in other tissues.

Analysis of the deduced amino acid sequence of the porcine CTR.

Analysis of the deduced amino acid sequence of the porcine CTR (FIG. 3) SEQ ID NO:1 revealed a molecule with an unusual structure. Searches of nucleic acid and protein sequence databases have not identified sequences similar to porcine CTR. A Kyte-Doolittle hydropathy analysis (Kyte and Doolittle, 1982, J. Mol. Biol. 157:105) indicated seven or eight regions of hydrophobic amino acid sequences that could generate transmembrane domains. The porcine CTR has no significant sequence identity (12%) to any of the approximately 120 cloned receptors that are thought to span the membrane seven times and to interact with G proteins (Attwood et al., 1991, Gene 98:153).

The $NH_2$-terminal hydrophobic domain, a putative hydrophobic signal sequence (Von Heijne, 1986, Nucl. Acids Res. 14:4683), precedes a long $NH_2$-terminal domain (147 amino acids with 3 potential N-linked glycosylation sites) that is presumed to be extracellular. There is a short cytosolic loop between helices V and VI that is not similar to corresponding regions of other adenylate cyclase-coupled receptors; this region is thought to couple to $G_{s\alpha}$. This unusual structural feature of the porcine CTR could account for the observed coupling of the receptor to different G proteins in cultured osteoclasts (Zadi et al., 1990, J. Endocrinol. 126:473) and the coupling that is observed during different phases of the cell cycle in $LLC-PK_1$ cells (Chakraborty et al., 1991, Science 251:1078). There is a striking degree of amino acid sequence similarity between the porcine CTR and the PTH-PTH related peptide (PTH-PTHrP) receptor, which is also different from other G-protein coupled receptors (FIG. 3; Juppner et al., 1991, Science 254:1024). Although the PTH-PTHrP receptor is more than 100 amino acids longer than the porcine CTR, there is an overall approximate 32% identity and an approximate 56% similarity between the sequences of the two receptors. A stretch of 17 out of 18 amino acids around the putative transmembrane domain VII are identical. Also, two out of four N-linked glycosylation sites and the position of seven out of eight potentially extracellular cysteines are conserved (FIG. 3). Major differences between the two receptors appear to lie in their N-terminal and carboxy-terminal domains, where gaps exist in the porcine CTR sequence relative to the PTH-PTHrP sequence. Both receptors also activate adenylate cyclase (FIG. 2; Juppner et al., 1991, Science 254:1024). The structural similarity of the porcine CTR and the PTH-PTHrP receptor suggests that they represent members of a new class of seven transmembrane-spanning G protein-coupled receptors that activate adenylate cyclase.

Cloning and Analysis of the cDNA Encoding a High Affinity Calcitonin Receptor from Human Cells.

A size-fractionated library with inserts greater than 2 kb in length consisting of 17 million recombinants was constructed from a rare small cell human ovarian carcinoma cell line, BIN-67, previously reported to respond to calcitonin with increases in cAMP (Upchurch et al., 1986, J. Bone and Mineral Res. 1:299). Poly $A^+$ mRNA was prepared from cells by the proteinase K/SDS method (Sambrook et al., 1989, Molecular Cloning. A Laboratory Manual, Cold Spring Harbor Laboratory Press, N.Y.) and purified by chromatography through oligo-dT cellulose (Collaborative Research, Bedford Mass.). The mRNA was converted to double stranded cDNA (Gubler and Hoffman, 1983, Gene 25:263) and after separation on a potassium acetate gradient (20%/5%), size-fractionated cDNA greater than 2 kb was ligated into the eukaryotic expression vector pcDNA-1 (Invitrogen, San Diego, Calif.). An aliquot of the ligated plasmid-cDNA library was electroporated into MC1061/P3 E. coli with a Bio-Rad Gene Pulser (Richmond, Calif.), using pulse conditions as follows: 200 ω, 2.5 kV, and 2.5 µF) in 0.2 cm gap cuvettes. The bacteria were then diluted and plated on 15 cm petri dishes containing selective agar. Two nylon filters (ICN, Cleveland, Ohio) were sequentially imprinted with plasmid-containing clones by placing them in contact with the bacterial colonies on the agar. The imprinted filters were screened by in situ hybridization as follows: The colonies were lysed by placing the filters face up on filter paper (Whatman No. 1) that was soaked with a solution containing 5% SDS in 2× standard saline citrate (SSC). Released DNA from the bacteria was denatured by heating at 650 watts for 2.5 minutes in a microwave oven. Filters were then washed in 5×SSC+0.1% SDS, followed by 5×SSC without SDS, and then transferred to microwave cooking bags (Kapak, Minneapolis, Minn.). Filters were prehybridized in 5×SSC; 40% formamide; 50 mM sodium phosphate; 5×Denhardts solution; sheared, denatured salmon sperm DNA (0.5 mg/ml) and 0.2% SDS. A radiolabeled cDNA probe was prepared from a 1100 base pair (bp) restriction fragment of the porcine CTR open reading frame as described above, using the Klenow fragment of prokaryotic DNA polymerase I (Pharmacia, Uppsala, Sweden), in the presence of random sequence hexanucleotides and [$\alpha^{32}P$] dCTP (New England Nuclear/Dupont, Boston, Mass.). Hybridization was carried out in a solution containing 5×SSC; 40% formamide, 20 mM sodium phosphate; 5×Denhardts solution; 0.1 mg/ml salmon sperm DNA and the radioactive probe for 12–24 hours. Following hybridization, filters were washed in 2×SSC+0.2% SDS at room temperature for 30 minutes followed by a second wash in 0.5×SSC+0.2% SDS at room temperature for 4 hours with multiple buffer changes. Autoradiography was performed by exposing the filters to Kodak XAR-5 film (Rochester, N.Y.) for 12–72 hours, with an intensifying screen. Colonies that hybridized with the labeled probe on both filters from a matching pair were isolated from the original agar plate, grown overnight, and the plasmid DNA they contained was isolated using an alkaline lysis procedure (Sambrook et al. Supra).

Approximately 55,000 colonies were transferred to nylon filters and screened to yield one positive clone which contained an insert of 3,605 bp. Positive clones were retested by Southern blot hybridization. A human cDNA clone, named HCTR-BIN67, which hybridized to the porcine cDNA restriction fragment probe was chosen for further study.

Sequencing of the Human CTR cDNA.

Restriction fragments of a CTR-containing cDNA clone were subcloned into M13 phage vectors mp18 and mp19 (Boehringer-Mannheim, Indianapolis, Ind.) for sequencing. Both strands were sequenced by the dideoxynucleotide chain termination procedure with modified T7 polymerase (United States Biochemical Corp., Cleveland, Ohio). The cloned plasmid containing the CTR cDNA was also used in some reactions for sequencing template DNA ("double-stranded" DNA sequencing). Complimentary oligonucleotides to the sequenced DNA were synthesized for use as sequencing primers using an oligonucleotide synthesizer.

Transfection of COS-M6 (COS-7 subclone) with human cTR cDNA.

Plasmid DNA was used to transfect COS-M6 cells growing in 10 cm petri dishes (Falcon, Lincoln Park, N.J.) using the DEAE-dextran/chloroquine procedure (Seed and Aruffo, 1987, Proc. Natl. Acad. Sci. USA 84:3365). Forty-eight hours after transfection, cells were incubated in the presence of either iodinated calcitonin for ligand binding studies, or unlabeled calcitonin for the assay of intracellular cAMP.

Binding of radiolabeled salmon and human calcitonin to cultured cells.

Human small ovarian cell carcinoma cells (BIN-67) were grown in 10 cm petri dishes in Dulbecco's modified Eagle's medium (DMEM) supplemented with 20% (vol/vol) heat inactivated fetal calf serum (GIBCO) and enriched with 25% Ham's F12 medium (GIBCO). Cells at near confluency, were passed approximately twice a week by trypsinization using 0.25% trypsin (GIBCO). Radioligand binding assays were performed in triplicate as follows. The cells were washed, trypsinized and counted in an automated cell counter (Coulter, Hialeah, Fla.). They were distributed into 12×75 mm glass tubes at $5 \times 10^5$ cells per tube in a volume of 200 µl of binding buffer [phosphate buffered saline (PBS), pH 7.4, 11 mM glucose, 0.5% bovine serum albumin] plus 200 pM of either [$^{125}$I]-salmon calcitonin (Peninsula Laboratory, Belmont, Calif.), or [$^{125}$I]-human calcitonin (Amersham, Arlington Heights, Ill.) in the presence of appropriate amounts of unlabeled ligand (Sigma, St. Louis, Mo.). The mixture was incubated for 14–16 hours at 4° C. The cells were washed by layering 100 µl of cell suspension over 400 µl of 10% sucrose (wt/vol) in a mini-microfuge tube (Bio-Rad) and centrifuging at maximum speed in a microfuge for three minutes to pellet the cells. The supernatant was removed by aspiration, and the portion of the tube containing the cell pellet was cut off and assayed for radioactive content in a gamma counter (TM Analytic, Elk Grove Village, Ill.). Ligand binding to COS-M6 cells transfected with a human CTR-containing plasmid was performed using the same technique.

cAMP assay.

BIN-67 cells or COS-M6 cells were grown in 10 cm petri dishes. Forty eight hours before the cAMP assay, the COS-M6 cells were transfected with either human CTR cDNA, or with β-galactosidase cDNA which served as a control. After 24 hours, the transfected COS-M6 cells and the BIN-67 cells were trypsinized and transferred to plastic trays containing 24 16 mm wells (Falcon) at an initial plating density of $5 \times 10^4$ cells/well. To test for hormone-induced cAMP responses, the medium was removed from each well and the cells were washed with PBS supplemented with calcium and magnesium. Triplicate groups of cells were incubated for 20 minutes at 37° C. at room temperature with either test buffer [PBS supplemented with calcium, magnesium, 0.25% bovine serum albumin, 11 mM glucose and 1 mM 3-isobutyl-methyl-xanthine (IBMX)], or with 4 mM isoproterenol or peptide hormone at the appropriate concentrations. Reactions were stopped by placing the culture plates in a water bath at 100° C. until all liquid had evaporated. The plates were stored at −20° C. until assayed. The cAMP assay was performed by adding 1.0 ml of 50 mM sodium acetate buffer, pH 6.2, to each well. Dried cells were scraped into this buffer, transferred to glass tubes and centrifuged at 500×g for 10 minutes. Aliquots of supernatant were assayed for cAMP using a radioimmunoassay kit (New England Nuclear/Dupont cAMP [$^{125}$I] Radioimmunoassay Kit, Dupont).

Emulsion autoradiography of BIN-67 cells.

Cells were grown on glass chamber slides (Nunc, Kamstrup, DK). The medium was removed by aspiration and the cells were incubated in binding buffer (PBS supplemented with 11 mM glucose, 0.5% bovine serum albumin) with [$^{125}$I]-salmon calcitonin (200 pM) with or without $10^{-6}$ M unlabeled salmon calcitonin (Sigma). After 5 washes in ice cold PBS supplemented with calcium and magnesium, the cells were fixed in PBS plus 2% formaldehyde, coated with Kodak NTB2 emulsion and exposed for 1–3 weeks at 4° C., after which they were developed and counterstained with Giemsa.

Northern blot hybridization analysis.

Samples containing 5 µg of poly A$^+$ RNA prepared from BIN-67 cells, T-47D cells (a human breast carcinoma cell line which expresses well characterized calcitonin receptors), and human giant cell tumor of bone tissue (hGCTu), and 1 µg of poly A$^+$ RNA prepared from LLC-PK$_1$ cells were electrophoresed on a 1% agarose gel containing formaldehyde and transferred by capillary action, using 10×SSC, to a supported nitrocellulose filter (Schleicher and Schuell). The filter was heated for 90 minutes at 80° C. under vacuum. Prehybridization was performed for 12–16 hours in 40% formamide (vol/vol); 5×SSC; 50 mM sodium phosphate, pH 7.2; 0.5 mg salmon sperm DNA per ml; 5×Denhardt's solution and 0.2% SDS. Hybridization was performed at 42° C. for 12–16 hours using a probe consisting of a human CTR cDNA Sac I digested restriction fragment of approximately 950 bp, labeled with [$\alpha^{32}$P]dCTP (New England Nuclear/Dupont) by random primer labeling. The hybridization solution contained 40% formamide; 5×SSC; 50 mM sodium phosphate; 5×Denhardt's solution and 0.1 mg/ml salmon sperm DNA. The filters were washed two times with 2×SSC, 0.2% SDS for 15 minutes at room temperature followed by four 20 minute washes in 0.2×SSC, 0.2% SDS at 60° C. Hybridized RNA was visualized following exposure of the filters to Kodak XAR-5 film for 24–72 hours at −70° C. with intensifying screen Characterization of Human CTRs in the BIN-67 cell line using [$^{125}$I]-salmon calcitonin emulsion autoradiography.

Figure 4A:
Figure 4B:

The BIN-67 cell line was isolated from a trypsin digest of a human metastatic pelvic nodule derived from a primary ovarian small cell carcinoma, a rare tumor composed of poorly differentiated cells of uncertain developmental origin (Upchurch et al., 1986, J. Bone and Mineral Res. 1:299; Dickersin et al., 1982, Cancer 49:188; Moll et al., 1983, Lab. Invest.49:599). The cultured cell line preserves the mixed character of the primary tumor with both large and small cell components. The small cells contain small dark nuclei with scanty cytoplasm which often grow in mounds on tissue culture plastic. Adjacent areas reveal larger cells with dense abundant cytoplasm and nuclei with prominent nucleoli. These cells grow with cytoplasmic extensions which spread out over the surface of the culture dish but do not tend to adhere closely to adjacent cells. FIG. 4A and 4B are two emulsion autoradiographs prepared from cells after incubation with [$^{125}$I]-salmon calcitonin. The presence of receptors for salmon calcitonin are indicated by the dense silver granules conforming to the outline of individual cells. In FIG. 4A it can be seen that the cells are clearly heterogeneous with respect to the expression of calcitonin receptors. FIG. 4B is a high power view of a cell which expresses abundant calcitonin receptors. The specificity of salmon calcitonin for these cells was demonstrated by the fact that incubation with excess unlabeled salmon calcitonin competed out all of the label.

Characterization of radioiodinated calcitonin binding in BIN-67 cells.

Figure 5A:
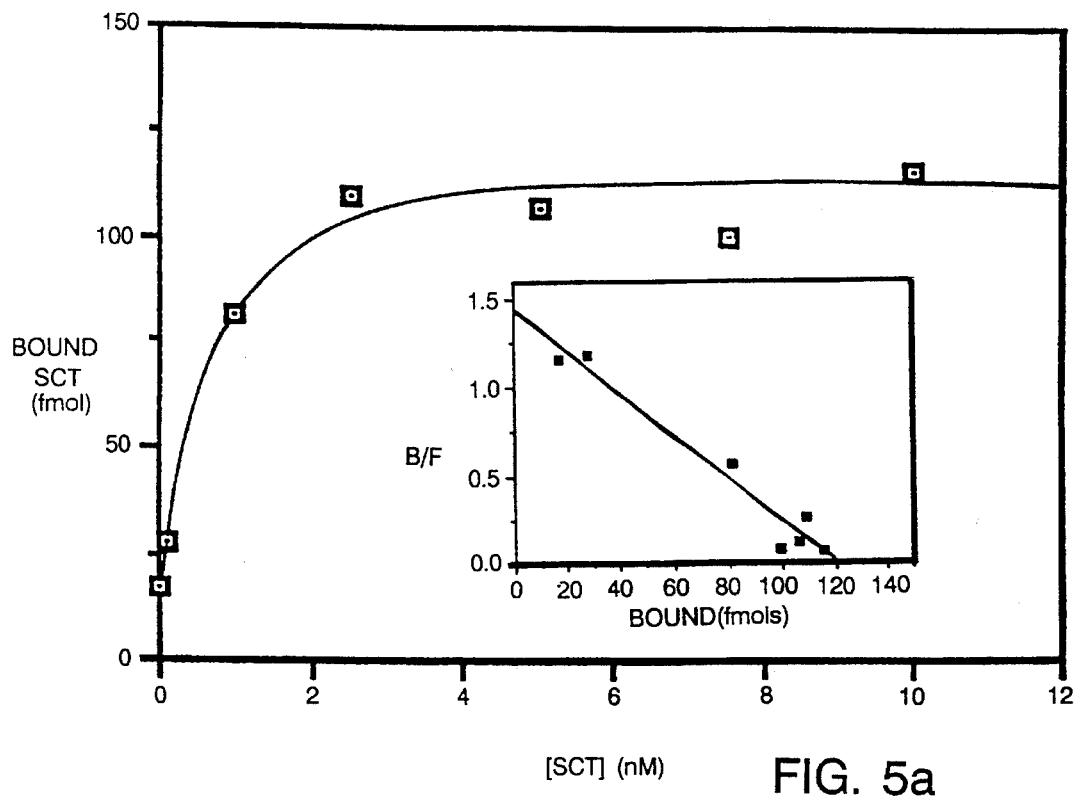
FIG. 5A is a graph of binding of salmon calcitonin to BIN-67 cells.

Scatchard analysis of binding data in BIN-67 cells using radiolabeled salmon calcitonin was consistent with a single class of high affinity calcitonin binding sites with a calculated $K_d$ of 0.42 nM (FIG. 5A). The average number of specific binding sites per cell was 143,000. Scatchard analysis of binding studies on BIN-67 cells using radiolabeled human calcitonin demonstrated a 10-fold lower affinity of these cells for human calcitonin with a $K_d$ of approximately 4.6 nM (FIG. 6C).

Analysis of data from competition dissociation studies following incubation of BIN-67 cells with [$^{125}$I]human calcitonin in the presence of increasing concentrations of unlabeled salmon calcitonin revealed an apparent 50% inhibitory concentration (IC$_{50}$) in the range of 0.6–0.7 nM (FIG. 6B). Parallel studies using [$^{125}$I]human calcitonin with increasing concentrations of unlabeled human calcitonin confirmed a 5–10-fold lower affinity (IC$_{50}$ approximately 3–7 nM) of BIN-67 cells for human calcitonin compared to salmon calcitonin (FIG. 6B). In addition, the peptide hormones, secretin and PTH, failed to displace radiolabeled salmon or human calcitonin binding even at concentrations as high as 10$^{-5}$ M. Additional studies confirmed that calcitonin binding sites were saturable with maximal binding at 4° C. occurring by approximately 12 hours.

Characterization of radioiodinated calcitonin binding to COS-M6 cells transfected with the human CTR cDNA.

Figure 5B:
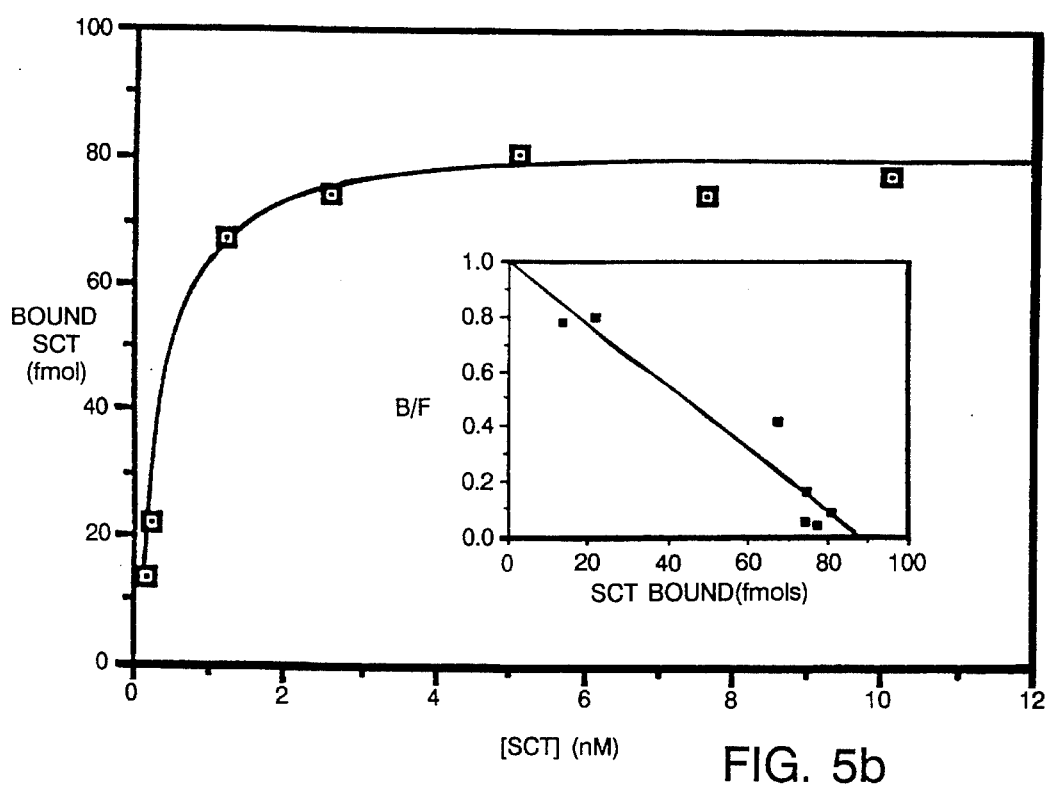
FIG. 5B is a graph of binding of salmon calcitonin to COS cells transfected with the human CTR cDNA. Insets show Scatchard analysis of binding data.

COS-M6 cells, which do not express CTR or CTR-like molecules on their cell surface, were transfected with the plasmid HCTR-BIN67 containing the human CTR cDNA and incubated with either radioiodinated salmon or human calcitonin. Scatchard analysis of binding data was consistent with the presence of a single class of high affinity calcitonin binding sites (FIG. 5B). Assuming 10% transfection efficiency (based on previous studies), the number of receptors per cell was approximately 1.4×10$^6$. The apparent K$_d$ for salmon calcitonin was 0.44 nM, which agrees closely with the apparent K$_d$ for this peptide in native BIN-67 cells (0.42 nM). As in the native cells, the expressed human CTR in COS-M6 cells had an approximate 10-fold lower affinity for human calcitonin (6.4 nM) compared to salmon calcitonin. The specificity of binding in COS cells transfected with the human CTR cDNA was indicated by the failure of other hormones, including PTH or secretin, to compete for binding with either radioiodinated salmon or human calcitonin.

Characterization of hormone-induced cAMP responses in BIN-67 cells and in COS-M6 cells transfected with the human CTR cDNA.

As shown in FIG. 7A, BIN-67 cells exhibited a dose-dependent increase in cAMP levels in response to salmon or human calcitonin. The 50% maximal effective concentrations (EC$_{50}$) for salmon calcitonin (approximately 0.7 nM) and human calcitonin (approximately 3.0 nM) illustrate the greater sensitivity of these cells to salmon calcitonin. These data are consistent with the dissociation constants for these peptides based on binding studies with radiolabeled ligands.

To determine whether the human CTR cDNA encoded a calcitonin binding protein that can couple to adenylate cyclase, COS-M6 cells were transfected with the human CTR cDNA and then incubated with calcitonin for 20 minutes in the presence of the phosphodiesterase inhibitor, IBMX. As shown in FIG. 7C, transfected cells had approximately a 4-fold increase in cAMP levels when incubated with maximal stimulatory concentrations of salmon calcitonin. The range was 2 to 4-fold in multiple experiments. This increase is considerably lower than the magnitude of the response in BIN-67 cells (approximately 9 to 24-fold, FIG. 7B). COS-M6 cells transfected with a β-galactosidase cDNA failed to increase cAMP levels above control levels following incubation with salmon calcitonin. The specificity of the salmon calcitonin-induced cAMP response was further demonstrated by the failure of PTH to induce a response (FIG. 7C), and by the fact that incubation with secretin at concentrations up to 10$^{-6}$ M also failed to induce a response. Finally, isoproterenol, an agonist of the β-adrenergic receptor, increased cAMP levels in both the mock-transfected and the human CTR-transfected COS cells.

Analysis of the human CTR cDNA predicted amino acid sequence.

Sequence analysis of the 3,605 bp human CTR cDNA (FIGS. 8.1–8.3) SEQ ID NO:2 revealed an open reading frame beginning at bp 250, which encodes a putative peptide of 490 amino acids. Comparison of this deduced amino acid sequence to that of the putative porcine CTR demonstrates a sequence identity of 73% and a similarity of 89%. The putative human CTR is eight amino acids longer than the peptide deduced from the porcine cDNA. The human CTR contains a second in frame AUG located at bp 195, or 55 bp upstream from the assigned start site. Both AUG codons have an A at the −3 position consistent with and sufficient for a consensus start site, although neither fits the strict consensus CC (A,G) CC AUG G (Kozak, 1984, Nucl. Acids Res. 12:857). An N-terminal domain encoded by the upstream AUG would contain mostly polar, hydrophilic residues and does not conform to the general outline of a signal peptide (von Heijne, 1986, Nucl. Acids Res. 14:4683). The downstream AUG, on the other hand, encodes a putative signal-like peptide, including a central hydrophobic domain (the h-region) flanked by polar regions consistent with the general outline of a signal peptide. The most likely cleavage site for this putative signal peptide falls between residues 22 and 23 (von Heijne, 1986, Nucl. Acids Res. 14:4683). The assignment of the human CTR cDNA start site to the downstream AUG at bp 250 is strongly supported by the positive alignment of identical and similar amino acid sequences, including a homologous N-terminal hydrophobic sequence encoded by the open reading frame of the porcine CTR cDNA (FIG. 1). The porcine CTR cDNA does not contain an analogous upstream start site to that of the human CTR cDNA, but instead possesses an in frame stop at 27 bp upstream from its start site.

When compared to other G protein-coupled hormone receptors, the deduced amino acid sequence of the human CTR shares many of the unusual structural features exhibited by the porcine CTR. A hydropathy plot (Kyte and Dolittle, 1982, J. Mol. Biol. 157:105) of the human CTR exhibits seven hydrophobic regions flanked by several charged residues which could form α-helical membrane spanning domains. The 22 residue putative signal sequence precedes a 124 amino acid presumed exoplasmic domain which includes three potential N-linked glycosylation sites that are conserved in the receptor from the two species. Both the human and porcine CTRs contain an unusual hydrophobic sequence near the carboxy-terminus consisting of a series of amino acids containing alanine as the predominant residue. This sequence is considerably shorter in the human CTR (amino acids 442–451) compared to the porcine sequence (amino acids 423–439) and is therefore not long enough to form a membrane spanning domain. Both CTRs possess an unusually short cytosolic loop between helices V and VI. In other G-protein coupled receptors, this region is thought to couple to G$_{s\alpha}$.

A major area of divergence between the human and porcine calcitonin receptors falls between the first and second transmembrane hydrophobic domains where the human CTR contains an inserted sequence of 16 consecutive amino acids not found in the porcine sequence (amino acids 176–191). This insert provides the human CTR with a longer intracellular loop between the first and second predicted transmembrane helices.

Searches of nucleic acid databases (Genbank and EMBL) and protein sequence databases (Genbank Translated Databases, PIR, and Swiss-Prot) identified the rat secretin receptor as the only published sequence which exhibits significant similarity to the human (or porcine) CTR. The recently cloned receptor for PTH-PTHrP (opossum kidney) is also similar to the human and porcine CTR (Juppner et al., 1991, Science 254:1024). A statistical analysis was performed at the National Center for Biotechnology Information (NCBI) using the BLAST network service (Altschul et al., 1990, J. Mol. Biol. 215:403) to compare the human CTR to the sequences in the database, including the approximately 120 receptor proteins with seven putative transmembrane domains thought to couple G-proteins. Sequence identity to members of this database, excluding the receptors for secretin and PTH, was less than 21%, with a Highest Scoring Hit Extension of 73 histogram units, compared to 163 units for secretin. The percent identity of the human CTR with either the PTH-PTHrP or secretin receptors is 34% with 58% similarity. The secretin receptor is 30% identical and 54% similar to the human CTR. The PTH and secretin receptors are even more closely related to each other with approximately 44% identity.

All of the related receptors human CTR, porcine CTR, PTH, PTH-PTHrP and secretin, possess homologous signal peptide-like N-terminal domains. The six cysteines in the human and porcine CTRs distal to the putative signal peptide site and proximal to the first membrane spanning domain are conserved without any gap required for their alignment. In the secretin receptor only four of the cysteine residues are conserved, diverging also at the cysteine residue just proximal to the first membrane spanning domain. In addition, two other extracellular cysteine residues are conserved at sites in the putative second and third extracellular domains of all three receptor types. Of the four potential N-linked glycosylation sites in the human N-terminal extracytoplasmic domain, three are conserved in the human and porcine CTRs; the distal two sites are also conserved in the CTRs and the PTH receptors. The secretin receptor preserves one N-linked glycosylation site nearest the first transmembrane domain, which is in a nearly identical position in the PTH and calcitonin receptors. This glycosylation site is displaced by only one amino acid toward the N-terminus relative to the first transmembrane domain in the secretin receptor compared to the PTH-PTHrP and CTR receptors.

The major areas of divergence in these receptors occurs in both the extracellular and cytoplasmic regions where gaps exist in the CTR and secretin receptor sequences relative to the longer PTH-PTHrP sequence. Nevertheless, some areas of sequence similarity and identity also exist in the C-terminal domains of these receptors all of which are known to be functionally coupled to adenylate cyclase (Murad et al., 1970, Proc. Natl. Acad. Sci. USA 65:446; Juppner et al., 1991 Science 254:1024; Ishihara et al., 1991, EMBO J. 10:1635).

RNA analysis.

Northern blot hybridization analysis using a human CTR cDNA probe was performed on RNA from BIN-67 cells and T-47D cells, and on RNA prepared from hGCTu cells. The hGCTu cells possess large numbers of multinucleated giant cells which express phenotypic features of osteoclasts, including the presence of calcitonin receptors (Goldring et al., 1987, J. Clin. Invest. 79:483). RNA from the porcine LLC-PK$_1$ cells was included as a reference. A single transcript of approximately 4.2 kb was evident in all of the samples (FIG. 9). The analysis was performed on the same blot under moderately stringent wash conditions (60° C. in 0.2×SSC). The extremely high levels of CTRmRNA in the LLC-PK$_1$ cells (they express approximately 3×10$^5$ CTRs per cell) were evident from the moderately labeled band seen in FIG. 9, when only one fifth of the mRNA was used compared to that used for the human cells despite the use of stringency conditions which were not optimized for species cross hybridization. Of the three human samples, BIN-67 and hGCTu cells contained much higher levels of CTR-specific mRNA than did T-47D cells.

Methods for Testing Compounds for Binding to the Human Calcitonin Receptor.

In the methods of the invention, compounds will be tested for their ability to bind to the calcitonin receptor, and for their ability to exhibit a biological activity of calcitonin. Calcitonin is currently used as a therapeutic agent to treat diseases characterized by abnormal bone-remodelling, including osteoporosis, Paget's disease of bone, and some forms of hypercalcemia associated with malignancy. A major disadvantage of calcitonin as a therapeutic agent is it's lack of oral availability. The invention provides methods for identification of compounds that bind to the calcitonin receptor and that exhibit biological activity of calcitonin. Large numbers of compounds can be tested using the methods of the invention. New or existing compounds that exhibit significant calcitonin activity in the assay may be orally available and treatment of humans with such compounds may therefore provide significant advantages to the patient over treatment with calcitonin.

Screening of compounds with potential CTR binding activity can be accomplished in a competition assay by incubating the receptor with labeled calcitonin and the compound to be tested under the standard binding conditions described above. If the compound binds to the CTR, calcitonin will be displaced from the CTR if already bound, or will be inhibited from binding to the CTR if not already bound. In either case, at the end of the incubation period, the amount of label associated with the receptor is an indication of the amount of calcitonin bound to the receptor and therefore an indication of the ability of the test compound to compete with calcitonin for binding.

With regard to the components of the assay, human and salmon calcitonin are available commercially and can be labeled with $^{125}$I or another suitable label such as biotin. The test compound is any newly synthesized compound or any available compound off the shelf. The receptor can be expressed on cell membranes, for example COS-M6 cells transfected with the cDNA encoding either porcine or human CTR. These cells can be transiently transfected with cDNA encoding CTR as described above, or can be stably transfected as follows: Cells can be cotransfected with the plasmid 3J8-14-F1 or HCTR-BIN67 and plasmid containing a selectable marker such as the neomycin resistance gene. Alternatively, 3J8-14-F1 or HCTR-BIN67 and a plasmid encoding neomycin resistance can be combined and the resulting construct can be transfected into cells. In either case, transfected cells are incubated in medium containing G418, such that only cells that are stably transformed to neomycin resistance will survive. These cells will also contain DNA sequences specifying human CTR. Cells that stably express the human CTR can be identified by the methods described above. This technology is common in the art and can be found in the Molecular Cloning Manual (Sambrook et al., Supra).

The invention is not limited to the use of COS-M6 cells in that any other cell line that does not express proteins that bind to calcitonin can also be used in the methods of the invention. The invention is also not limited to plasmids encoding porcine or human CTR; rather, any plasmid encoding a calcitonin receptor can be used.

The receptor can also be used in soluble cell-free form as described below. The cDNA encoding porcine or human CTR can be expressed under the control of inducible promoter/enhancer sequences that when activated, drive the expression of high levels of CTR following transfection of the construct into the appropriate cells. Methods of inducing high levels of expression of a protein in cells are common in the art and can be found for example in the Molecular Cloning Manual (Sambrook et al. Supra). Receptor molecules can be purified from the transfected cells using commonly available biochemical techniques, including affinity chromatography using a column containing bound calcitonin analog(s) which can be coupled to a matrix without loss of binding activity.

Alternatively, the cDNA encoding porcine or human CTR can be cloned into a baculovirus expression system, using technology that is standard in the art (e.g., Summers and Smith, 1987, A Manual of Methods for Baculovirus Vectors and Insect Cell Procedures. Texas Agricultural Experiment Station, Bulletin 1555, Texas A&M University, College Station, Tex.). Receptors expressed in this way can be purified as described above.

Following incubation of the components in the standard binding assay, unbound receptor or receptor that has bound to it calcitonin or the test compound can be isolated from unbound components by taking advantage of its differential solubility in the presence of polyethylene glycol. High molecular weight receptor molecules are selectively precipitated in a solution of polyethylene glycol. For example, an identical method has been successfully used to purify the insulin receptor (Marshall et al., 1985, J. Biol. Chem. 260:4128). The precipitate can be removed from unbound material by centrifugation and the amount of radioactivity in the precipitate can be measured in a gamma counter.

The methods described above therefore provide a useful screening procedure for the identification of compounds that bind calcitonin receptor. To identify compounds that also exhibit biological activity of calcitonin, COS-M6 cells, or any other cell line that does not express proteins on their surface that bind to calcitonin, are transfected with the cDNA encoding CTR. Test compounds or human or salmon calcitonin which serve as a controls, can be added to these cells and the mixture is incubated under the standard binding assay conditions as described above. Following incubation, cells are harvested and the levels of intracellular cAMP will be measured as described. An increase in the intracellular cAMP content in cells treated with the test compound that is similar to the increase in cAMP levels when the cells are treated with calcitonin, is an indication that the test compound exhibits a biological activity of calcitonin.

A second test for biological activity involves the use of the calcium sensitive dye fura-2-acetoxymethyl ester (Molecular Probes). This dye alters its fluorescent pattern when bound to calcium. When cells are treated with calcitonin, they exhibit an increase in calcium content. Thus, cells incubated in the presence of both calcitonin and the dye will have a different fluorescent pattern than cells that are not treated with calcitonin. If a test compound exhibits this biological activity of calcitonin when added to COS-M6 cells transfected with a cDNA encoding CTR in the presence of fura-2-acetoxymethyl ester, these cells should also exhibit altered fluorescence compared to untreated cells.

Antibodies and Probes Specific for the Calcitonin Receptor.

The invention also features antibodies and probes specific for CTR. Such antibodies or probes can be used for a variety of purposes including the location of other CTRs within tissues in a mammal which may provide insight into additional functions of calcitonin in mammals, and more importantly as a diagnostic tool, wherein cells that are associated with disease and that express CTRs on their surface can be identified.

Antibodies specific for the CTR can be generated in several ways. The procedures described below use as an example, the human CTR, but are not limited solely to the use of human CTR.

1) COS-M6 cells transfected with cDNA encoding human CTR (SEQ ID NO:2) as described above, can be used to immunize a rabbit or other mammal. These cells express human CTR on their surface but do not express other proteins with structural similarity to human CTR. Serum from inoculated rabbits can be obtained periodically and polyclonal antibody to human CTR contained therein can be purified using common techniques available in the art such as those described in Sambrook et al. (Supra).

2) Another method useful for the generation of antibodies involves cloning the cDNA encoding human CTR (SEQ ID NO:2) into a bacterial expression vector such that the CTR sequences are in frame with a bacterial gene, for example β-galactosidase. Bacteria that are transformed with such a construct will produce a fusion protein comprising human CTR and β-galactosidase. The fusion protein can be used to immunize a rabbit or other mammal that will then synthesize antibody specific for both proteins. This technology is also common in the art and is taught in Sambrook et al. (Supra).

3) Antibodies can also be generated in a rabbit or other mammal using as antigens peptides that are synthesized in a peptide synthesizer. The amino acid sequence of these peptides is identical to the amino acid sequence of the CTR deduced from the cDNA sequence described above. Such technology is also common in the art and is described in Sambrook et al. (Supra).

4) Human CTR that is purified according to the methods described above can also be used as an antigen for the generation of antibodies in a rabbit or other mammal.

The antibody can be used as a diagnostic tool to locate diseased cells that express calcitonin receptor using any of the methods for such purposes that are available in the art. For example, immunofluorescent or radioactive labeling techniques can be performed on tissues or individual cells as a means to identify cells, or to sort cells that express calcitonin receptor.

The antibody can also be used to screen bacterial expression libraries for the presence of calcitonin receptor, or for molecules that are related to the calcitonin receptor for example, CGRP or amylin receptor. Bacterial expression libraries specific for individual tissues are available, or can be made using the standard technology described in Sambrook et al. (Supra). Methods for screening such libraries using an antibody are also described in Sambrook et al (Supra).

In a manner similar to that described above, a probe specific for calcitonin receptor can be used as a diagnostic tool or to screen bacterial expression libraries specific for tissues for the expression of a calcitonin receptor. This can be accomplished using the methods described above or using any other conventional techniques e.g., those described in Sambrook et al. (Supra). The probe is the calcitonin receptor-encoding sequence or a calcitonin receptor-specific probe that contains at least 30 base pairs that are unique to the calcitonin receptor gene. Such sequences can be easily identified using a sequence data base and a computer.

DNA from bacteria that express calcitonin receptor molecules can be isolated using the methods described in the invention. This DNA can be tested in the transfection assays described above for the expression of receptors that bind calcitonin. Expressed receptors can also be tested in the cAMP assay described above to determine whether they are coupled to adenylate cyclase.

The identification and subsequent isolation of DNA encoding tissue-specific calcitonin receptors is an important aspect of the invention, because it allows for the screening of compounds that specifically bind to these receptors. It is likely that not all calcitonin receptors in a mammal are identical in their structure and in their biological function. Furthermore, it is important to identify and characterize calcitonin receptor-related molecules in individual tissues because these molecules may play important roles in the biological function of calcitonin or related peptides. Receptors so identified can also be used in the assay described above for the identification of yet other compounds that bind to such receptors because compounds that are effective in one tissue may not be equally effective in another tissue.

Deposit

The plasmid HCTR-BIN67, has been deposited with the American Type Culture Collection on Nov. 14, 1991, and bears the accession number ATCC No. 75144. Applicants acknowledge their responsibility to replace should the plasmid loose viability before the end of the term of a patent issued hereon, and their responsibility to notify the American Type Culture Collection of the issuance of such a patent, at which time the deposit will be made available to the public. Prior to that time the deposit will be made available to the Commissioner of Patents under the terms of CFR §1.14 and 35 USC §112.

What is claimed is:

1. A recombinant DNA consisting of a DNA sequence that encodes a calcitonin receptor polypeptide having the amino acid sequence set forth in SEQ ID NO: 1.

2. A recombinant DNA consisting of a DNA sequence that encodes a calcitonin receptor polypeptide having the amino acid sequence set forth in SEQ ID NO: 2.

3. The recombinant DNA of claim 1 or 2, wherein said DNA is CDNA.

4. A vector comprising the recombinant DNA of claim 1 or 2, said vector being capable of directing the expression of the polypeptide encoded by said DNA in a vector-containing cell.

5. The vector of claim 4, wherein said vector is the plasmid HCTR-BIN67.

6. A cell which contains the recombinant DNA of claim 1 or 2.

7. The cell of claim 6, said cell being a eukaryotic cell.

8. The cell of claim 7, said cell being a mammalian cell.

9. The cell of claim 8, said cell being a COS cell.

10. A method of producing a recombinant calcitonin receptor polypeptide, said method comprising, a) providing a cell transformed with the vector of claim 4, said vector being positioned for expression in said cell;

b) culturing said transformed cell under conditions for expressing said DNA; and c) isolating said recombinant calcitonin polypeptide.

* * * * *

UNITED STATES PATENT AND TRADEMARK OFFICE
CERTIFICATE OF CORRECTION

PATENT NO.   : 5,516,651

DATED        : May 14, 1996

INVENTOR(S)  : Steven R. Goldring, Alan H. Gorn, and Herb Y. Lin

It is certified that error appears in the above-identified patent and that said Letters Patent is hereby corrected as shown below:

Column 4, line 37, replace "3JS" with --3J8--;

Column 7, line 3, replace "Human small ovarian cell carcinoma cells (BIN-67) were" with --Human small cell ovarian carcinoma cells (BIN-67) were--;

Column 16, line 9, replace "loose" with --lose--;

Column 23, line 25, claim 3, replace "CDNA" with --cDNA--.

Signed and Sealed this

Twenty-seventh Day of August, 1996

Attest:

BRUCE LEHMAN

*Attesting Officer*   *Commissioner of Patents and Trademarks*

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
( A ) LENGTH: 482
( B ) TYPE: amino acid
( C ) STRANDEDNESS: Not Relevant
( D ) TOPOLOGY: Not Relevant ( x i ) SEQUENCE DESCRIPTION: SEQ ID NO: 1:

```
Met Arg Phe Thr Leu Thr Arg Trp Cys Leu Thr Leu Phe Ile Phe Leu
              5                   10                  15

Asn Arg Pro Leu Pro Val Leu Pro Asp Ser Ala Asp Gly Ala His Thr
            20                  25                  30

Pro Thr Leu Glu Pro Glu Pro Phe Leu Tyr Ile Leu Gly Lys Gln Arg
            35                  40                  45

Met Leu Glu Ala Gln His Arg Cys Tyr Asp Arg Met Gln Lys Leu Pro
    50                  55                  60

Pro Tyr Gln Gly Glu Gly Leu Tyr Cys Asn Arg Thr Trp Asp Gly Trp
65                      70                  75                  80

Ser Cys Trp Asp Asp Thr Pro Ala Gly Val Leu Ala Glu Gln Tyr Cys
                    85                  90                  95

Pro Asp Tyr Phe Pro Asp Phe Asp Ala Ala Glu Lys Val Thr Lys Tyr
                100                 105                 110

Cys Gly Glu Asp Gly Asp Trp Tyr Arg His Pro Glu Ser Asn Ile Ser
            115                 120                 125

Trp Ser Asn Tyr Thr Met Cys Asn Ala Phe Thr Pro Asp Lys Leu Gln
    130                 135                 140

Asn Ala Tyr Ile Leu Tyr Tyr Leu Ala Ile Val Gly His Ser Leu Ser
145                 150                 155                 160

Ile Leu Thr Leu Leu Ile Ser Leu Gly Ile Phe Met Phe Leu Arg Ser
                165                 170                 175

Ile Ser Cys Gln Arg Val Thr Leu His Leu Asn Met Phe Leu Thr Tyr
            180                 185                 190

Val Leu Asn Ser Ile Ile Ile Ile Val His Leu Val Val Ile Val Pro
            195                 200                 205

Asn Gly Glu Leu Val Lys Arg Asp Pro Pro Ile Cys Lys Val Leu His
    210                 215                 220

Phe Phe His Gln Tyr Met Met Ser Cys Asn Tyr Phe Trp Met Leu Cys
```

| 225 | | | | | | 230 | | | | | | 235 | | | | | | 240 | |
|---|---|---|---|---|---|---|---|---|---|---|---|---|---|---|---|---|---|---|---|
| Glu | Gly | Val | Tyr | Leu<br>245 | His | Thr | Leu | Ile | Val<br>250 | Val | Ser | Val | Phe | Ala<br>255 | Glu | | | | |
| Gly | Gln | Arg | Leu<br>260 | Trp | Trp | Tyr | His | Val<br>265 | Leu | Gly | Trp | Gly | Phe<br>270 | Pro | Leu | | | | |
| Ile | Pro | Thr<br>275 | Thr | Ala | His | Ala | Ile<br>280 | Thr | Arg | Ala | Val | Leu<br>285 | Phe | Asn | Asp | | | | |
| Asn | Cys<br>290 | Trp | Leu | Ser | Val | Asp<br>295 | Thr | Asn | Leu | Leu | Tyr<br>300 | Ile | Ile | His | Gly | | | | |
| Pro<br>305 | Val | Met | Ala | Ala | Leu<br>310 | Val | Val | Asn | Phe | Phe<br>315 | Phe | Leu | Leu | Asn | Ile<br>320 | | | | |
| Leu | Arg | Val | Leu | Val<br>325 | Lys | Lys | Leu | Lys | Glu<br>330 | Ser | Gln | Glu | Ala | Glu<br>335 | Ser | | | | |
| His | Met | Tyr | Leu<br>340 | Lys | Ala | Val | Arg | Ala<br>345 | Thr | Leu | Ile | Leu | Val<br>350 | Pro | Leu | | | | |
| Leu | Gly | Val<br>355 | Gln | Phe | Val | Val | Leu<br>360 | Pro | Trp | Arg | Pro | Ser<br>365 | Thr | Pro | Leu | | | | |
| Leu | Gly<br>370 | Lys | Ile | Tyr | Asp | Tyr<br>375 | Val | Val | His | Ser | Leu<br>380 | Ile | His | Phe | Gln | | | | |
| Gly<br>385 | Phe | Phe | Val | Ala | Ile<br>390 | Ile | Tyr | Cys | Phe | Cys<br>395 | Asn | His | Glu | Val | Gln<br>400 | | | | |
| Gly | Ala | Leu | Lys | Arg<br>405 | Gln | Trp | Asn | Gln | Tyr<br>410 | Gln | Ala | Gln | Arg | Trp<br>415 | Ala | | | | |
| Gly | Arg | Arg | Ser<br>420 | Thr | Arg | Ala | Ala | Asn<br>425 | Ala | Ala | Ala | Thr<br>430 | Ala | Ala | | | | | |
| Ala | Ala | Ala<br>435 | Ala | Leu | Ala | Glu | Thr<br>440 | Val | Glu | Ile | Pro | Val<br>445 | Tyr | Ile | Cys | | | | |
| His | Gln<br>450 | Glu | Pro | Arg | Glu | Glu<br>455 | Pro | Ala | Gly | Glu | Glu<br>460 | Pro | Val | Val | Glu | | | | |
| Val<br>465 | Glu | Gly | Val | Glu | Val<br>470 | Ile | Ala | Met | Glu | Val<br>475 | Leu | Glu | Gln | Glu | Thr<br>480 | | | | |
| Ser | Ala | | | | | | | | | | | | | | | | | | |

( 2 ) INFORMATION FOR SEQ ID NO: 2:

( i ) SEQUENCE CHARACTERISTICS:
        ( A ) LENGTH: 3588
        ( B ) TYPE: nucleic acid
        ( C ) STRANDEDNESS: double
        ( D ) TOPOLOGY: linear ( x i ) SEQUENCE DESCRIPTION: SEQ ID NO: 2:

```
GTGCGCACGT  CCGCACCTCA  CCCTGCGGCT  GACATCTCCT  GCCCAGGAGA  TGGGCGCTGA      60

AGCTTGAGCG  CCTGAGTCCC  TGGAGCCACA  CCTGCGAACA  CCCTTTGCTT  CTATTGAGCT     120

GTGCCCAGCC  GCCCAGTGAC  AGAATTCCAG  AATAAATGAT  TCCCACTGAT  CCACCCACTT     180

TTGCCACCCC  AGGATGCAAT  TTTCTGGAGA  GAAGATTAGT  GGACAAAGAG  ATCTTCAAAA     240

ATCAAAA                                                                   247
```

| ATG | AGG | TTC | ACA | TTT | ACA | AGC | CGG | TGC | TTG | GCA | CTG | TTT | CTT | CTT | CTA | 295 |
|---|---|---|---|---|---|---|---|---|---|---|---|---|---|---|---|---|
| Met<br>1 | Arg | Phe | Thr | Phe<br>5 | Thr | Ser | Arg | Cys | Leu<br>10 | Ala | Leu | Phe | Leu | Leu<br>15 | Leu | |

| AAT | CAC | CCA | ACC | CCA | ATT | CTT | CCT | GCC | TTT | TCA | AAT | CAA | ACC | TAT | CCA | 343 |
|---|---|---|---|---|---|---|---|---|---|---|---|---|---|---|---|---|
| Asn | His | Pro | Thr<br>20 | Pro | Ile | Leu | Pro | Ala<br>25 | Phe | Ser | Asn | Gln | Thr<br>30 | Tyr | Pro | |

| ACA | ATA | GAG | CCC | AAG | CCA | TTT | CTT | TAC | GTC | GTA | GGA | CGA | AAG | AAG | ATG | 391 |
|---|---|---|---|---|---|---|---|---|---|---|---|---|---|---|---|---|
| Thr | Ile | Glu | Pro | Lys<br>35 | Pro | Phe | Leu | Tyr | Val<br>40 | Val | Gly | Arg | Lys | Lys<br>45 | Met | |

```
                    35                        40                            45
ATG GAT GCA CAG TAC AAA TGC TAT GAC CGA ATG CAG CAG TTA CCC GCA            439
Met Asp Ala Gln Tyr Lys Cys Tyr Asp Arg Met Gln Gln Leu Pro Ala
    50                  55                  60

TAC CAA GGA GAA GGT CCA TAT TGC AAT CGC ACC TGG GAT GGA TGG CTG            487
Tyr Gln Gly Glu Gly Pro Tyr Cys Asn Arg Thr Trp Asp Gly Trp Leu
65                      70                  75                  80

TGC TGG GAT GAC ACA CCG GCT GGA GTA TTG TCC TAT CAG TTC TGC CCA            535
Cys Trp Asp Asp Thr Pro Ala Gly Val Leu Ser Tyr Gln Phe Cys Pro
                85                      90                  95

GAT TAT TTT CCG GAT TTT GAT CCA TCA GAA AAG GTT ACA AAA TAC TGT            583
Asp Tyr Phe Pro Asp Phe Asp Pro Ser Glu Lys Val Thr Lys Tyr Cys
            100                     105                 110

GAT GAA AAA GGT GTT TGG TTT AAA CAT CCT GAA AAC AAT CGA ACC TGG            631
Asp Glu Lys Gly Val Trp Phe Lys His Pro Glu Asn Asn Arg Thr Trp
        115                     120                 125

TCC AAC TAT ACT ATG TGC AAT GCT TTC ACT CCT GAG AAA CTG AAG AAT            679
Ser Asn Tyr Thr Met Cys Asn Ala Phe Thr Pro Glu Lys Leu Lys Asn
    130                     135                 140

GCA TAT GTT CTG TAC TAT TTG GCT ATT GTG GGT CAT TCT TTG TCA ATT            727
Ala Tyr Val Leu Tyr Tyr Leu Ala Ile Val Gly His Ser Leu Ser Ile
145                     150                 155                 160

TTC ACC CTA GTG ATT TTC CTG GGG ATT TTC GTG TTT TTC AGA AAA TTG            775
Phe Thr Leu Val Ile Phe Leu Gly Ile Phe Val Phe Phe Arg Lys Leu
                165                     170                 175

ACA ACT ATT TTT CCT TTG AAT TGG AAA TAT AGG AAG GCA TTG AGC CTT            823
Thr Thr Ile Phe Pro Leu Asn Trp Lys Tyr Arg Lys Ala Leu Ser Leu
            180                     185                 190

GGC TGC CAA AGG GTA ACC CTG CAC AAG AAC ATG TTT CTT ACT TAC ATT            871
Gly Cys Gln Arg Val Thr Leu His Lys Asn Met Phe Leu Thr Tyr Ile
        195                     200                 205

CTG AAT TCT ATG ATT ATC ATC ATC CAC CTG GTT GAA GTA GTA CCC AAT            919
Leu Asn Ser Met Ile Ile Ile Ile His Leu Val Glu Val Val Pro Asn
    210                     215                 220

GGA GAG CTC GTG CGA AGG GAC CCG GTG AGC TGC AAG ATT TTG CAT TTT            967
Gly Glu Leu Val Arg Arg Asp Pro Val Ser Cys Lys Ile Leu His Phe
225                     230                 235                 240

TTC CAC CAG TAC ATG ATG GCC TGC AAC TAT TTC TGG ATG CTC TGT GAA           1015
Phe His Gln Tyr Met Met Ala Cys Asn Tyr Phe Trp Met Leu Cys Glu
                245                     250                 255

GGG ATC TAT CTT CAT ACA CTC ATT GTC GTG GCT GTG TTT ACT GAG AAG           1063
Gly Ile Tyr Leu His Thr Leu Ile Val Val Ala Val Phe Thr Glu Lys
            260                     265                 270

CAA CGC TTG CGG TGG TAT TAT CTC TTG GGC TGG GGG TTC CCG CTG GTG           1111
Gln Arg Leu Arg Trp Tyr Tyr Leu Leu Gly Trp Gly Phe Pro Leu Val
        275                     280                 285

CCA ACC ACT ATC CAT GCT ATT ACC AGG GCC GTG TAC TTC AAT GAC AAC           1159
Pro Thr Thr Ile His Ala Ile Thr Arg Ala Val Tyr Phe Asn Asp Asn
    290                     295                 300

TGC TGG CTG AGT GTG GAA ACC CAT TTG CTT TAC ATA ATC CAT GGA CCT           1207
Cys Trp Leu Ser Val Glu Thr His Leu Leu Tyr Ile Ile His Gly Pro
305                     310                 315                 320

GTC ATG GCG GCA CTT GTG GTC AAT TTC TTC TTT TTG CTC AAC ATT GTC           1255
Val Met Ala Ala Leu Val Val Asn Phe Phe Phe Leu Leu Asn Ile Val
                325                     330                 335

CGG GTG CTT GTG ACC AAA ATG AGG GAA ACC CAT GAG GCG GAA TCC CAC           1303
Arg Val Leu Val Thr Lys Met Arg Glu Thr His Glu Ala Glu Ser His
            340                     345                 350

ATG TAC CTG AAG GCT GTG AAG GCC ACC ATG ATC CTT GTG CCC CTG CTG           1351
Met Tyr Leu Lys Ala Val Lys Ala Thr Met Ile Leu Val Pro Leu Leu
```

355                         360                         365

GGA ATC CAG TTT GTC GTC TTT CCC TGG AGA CCT TCC AAC AAG ATG CTT    1399
Gly Ile Gln Phe Val Val Phe Pro Trp Arg Pro Ser Asn Lys Met Leu
    370                 375                 380

GGG AAG ATA TAT GAT TAC GTG ATG CAC TCT CTG ATT CAT TTC CAG GGC    1447
Gly Lys Ile Tyr Asp Tyr Val Met His Ser Leu Ile His Phe Gln Gly
385                     390                 395                 400

TTC TTT GTT GCG ACC ATC TAC TGC TTC TGC AAC AAT GAG GTC CAA ACC    1495
Phe Phe Val Ala Thr Ile Tyr Cys Phe Cys Asn Asn Glu Val Gln Thr
                405                 410                 415

ACC GTG AAG CGC CAA TGG GCC CAA TTC AAA ATT CAG TGG AAC CAG CGT    1543
Thr Val Lys Arg Gln Trp Ala Gln Phe Lys Ile Gln Trp Asn Gln Arg
            420                 425                 430

TGG GGG AGG CGC CCC TCC AAC CGC TCT GCT CGC GCT GCA GCC GCT GCT    1591
Trp Gly Arg Arg Pro Ser Asn Arg Ser Ala Arg Ala Ala Ala Ala Ala
        435                 440                 445

GCG GAG GCT GGC GAC ATC CCA ATT TAC ATC TGC CAT CAG GAG CCG AGG    1639
Ala Glu Ala Gly Asp Ile Pro Ile Tyr Ile Cys His Gln Glu Pro Arg
    450                 455                 460

AAT GAA CCA GCC AAC AAC CAA GGC GAG GAG AGT GCT GAG ATC ATC CCT    1687
Asn Glu Pro Ala Asn Asn Gln Gly Glu Glu Ser Ala Glu Ile Ile Pro
465                 470                 475                 480

TTG AAT ATC ATA GAG CAA GAG TCA TCT GCT                            1717
Leu Asn Ile Ile Glu Gln Glu Ser Ser Ala
                485                 490

TGAATGTGAA GCAAACACAG TATCGTGATC ACTGAGCCAT CATTTCCTGG GAGAAAGACC 1777
ATGCATTTAA AGTATTCTCC ATCCTCCCAG GAACCGAACA TATCATTTGT GAAGAATTAT 1837
TCAGTGAATT TGTCCATTGT AAATCTGAAG AAAGTTATTC TTGGTACTGT TGCTTTGGGA 1897
GACAGTCTAG GAATGGAGTC TCCCACTGCA ACTTGTGAAC TCCATCATTC ATCCAGGACT 1957
GAGATGCAAA TGTCACAGTA ATGCAAGCAA AGTATCAAAG AAAAACAATG AAATTGACCT 2017
AGTTCAGATA CAGGGTGCTC CTTGTCAATA CTGAGCCATT TATACCTTTG AAATATTAAA 2077
ATCACTGTCA ATATTTTTAT TTTTAACTCT GGATTTTGAA TTAGATTATT TCTGTATTTG 2137
GCTATGGATC TGATTTTTAA TTTTTTTAAA TTTCAGTCAA TTCTGATGTT ACTGAGATGT 2197
TTACCATCC TTACAATGTA AACCACATGA ACTACGTGAC CTCTGCAAGA CAAAGCGGCT 2257
TTCTAATAGA GAGATTAGTA AATATGTGAA GAAAAAGACC TGCATTTGGC AGGAAGATGT 2317
ATGCTTTGAA TGCAAAAGAA ATTTAGAGTC AATTTGCTGA AAACATTACA TGCTCAGCTT 2377
GGTTTTGGAC AAGCCTGTCC ATTGGGCAGG ACCTAGCTGT TGTAAAGAAT TGGTCTTAAT 2437
GTTGAATGTA TTTTGGTTGC TGATGTTTAT AAACTGAGAG GTCACAAAGA ATCTATCACT 2497
AAAATTTTT ACAAACTGC CAAAATATA ATTCTTAGTG GAAGACAATA CTCCCTTTAA 2557
AGAAAGAGAG TTTGCCACTC CCCTAAACTC CAGGATTTAT AAAGCAAATT ACTCCAAGGT 2617
TTATAAAGCA GATTACCTCT TGCCCTTGGG TGCTATCTAG CAGTAAAAGA TAAATTTGTT 2677
GAATATTGGT AATTAAAAGA CTCCACATAA GTCCATTAAC TGCTTTCCAC CCAGCTTCAA 2737
AGCTTAAAAA GAGCTCAGGC TTTTCCAGGA AGATCCAGGA CGGCTAATTA GAAATCAACT 2797
TGTGGTTGAC CGCTTGTTTC TTGTTATTAC CAAAACAGGA GGGGAAAAAA TTAACTGCTC 2857
CAAATTTAAC CATAAATCAA TTCATGTTTA ACGTTTCTCA TTAAAATCCA GTATTATATT 2917
ATCATATCTC TCTTTACTTC CCAGTATAAG ATTTTTGAAA ATCCTGAATA AACCAGTATC 2977
GTTACTGGCA CCTGAAATTA ATTTGTGAAT TTGCAACAGT AATCAGAGTT ACCATTATTT 3037
AATTTGTATG CTAAATGAGG AGGTACATTG AAACCCTCCA AATCTCCAGT CTCATCTATG 3097

-continued

| | | | | | | |
|---|---|---|---|---|---|---|
| TCATATTTTG | CCACTGCCTT | TCAGAAGTGA | TTTAGTTGTG | GAAAGATAAT | AAATTGATTT | 3157 |
| GTTATGGTTA | CATATTCAGC | GCACGCAGAG | AAAATTAATT | ATATTTCTAC | AGAGAAAATG | 3217 |
| AATTTGGGAT | ACTAAAGTAG | TTTAAGTCTC | CTTTACTGAA | TGTAAGGGGG | GGATCGAAAA | 3277 |
| GAAGGTATTT | TTCCAATCAC | AGTGTTATGT | AGTATTGTTC | TATTTTTGTT | TACAAACATG | 3337 |
| GAAAACAGAG | TATTTCTGGC | AGCTCTCGTA | CAAATGTGAT | AATATATTGC | TAAAATATTT | 3397 |
| TAGATGTTAT | TATGCTAATA | TAGTAGGGGT | TGAAGAAAAC | AAAATAGCTT | ATTATAGAAT | 3457 |
| TGCACATAGT | TCTGCCCAAA | TTATGTGAAA | TGCTTATGCT | TGTGTATATG | TATAAATTAA | 3517 |
| TACACACTAC | GTTAAAAGCA | AAAAGATGTA | TATTTGCATA | TTTTCTAAA | GAAATATATT | 3577 |
| ATTCATCTTT | T | | | | | 3588 |